United States Patent
Emanuel

(10) Patent No.: US 10,758,639 B2
(45) Date of Patent: Sep. 1, 2020

(54) METHODS FOR THE TREATMENT OF PERI-IMPLANTITIS

(71) Applicant: POLYPID LTD., Petach Tikva (IL)

(72) Inventor: Noam Emanuel, Rehovot (IL)

(73) Assignee: Polypid Ltd., Petach-Tikva (IL)

( * ) Notice: Subject to any disclaimer, the term of this patent is extended or adjusted under 35 U.S.C. 154(b) by 0 days.

(21) Appl. No.: 15/513,163

(22) PCT Filed: Sep. 27, 2015

(86) PCT No.: PCT/IB2015/057410
§ 371 (c)(1),
(2) Date: Mar. 22, 2017

(87) PCT Pub. No.: WO2016/051322
PCT Pub. Date: Apr. 7, 2016

(65) Prior Publication Data
US 2017/0246342 A1 Aug. 31, 2017

Related U.S. Application Data

(60) Provisional application No. 62/059,116, filed on Oct. 2, 2014.

(51) Int. Cl.
| | |
|---|---|
| *A61L 27/12* | (2006.01) |
| *A61K 6/58* | (2020.01) |
| *A61K 31/65* | (2006.01) |
| *A61L 27/34* | (2006.01) |
| *A61K 33/06* | (2006.01) |
| *A61K 6/831* | (2020.01) |
| *A61K 6/849* | (2020.01) |
| *A61K 6/864* | (2020.01) |
| *A61K 6/891* | (2020.01) |
| *A61L 27/18* | (2006.01) |
| *A61L 27/54* | (2006.01) |
| *A61L 27/58* | (2006.01) |

(52) U.S. Cl.
CPC .............. *A61L 27/12* (2013.01); *A61K 6/58* (2020.01); *A61K 6/831* (2020.01); *A61K 6/849* (2020.01); *A61K 6/864* (2020.01); *A61K 6/891* (2020.01); *A61K 31/65* (2013.01); *A61K 33/06* (2013.01); *A61L 27/18* (2013.01); *A61L 27/34* (2013.01); *A61L 27/54* (2013.01); *A61L 27/58* (2013.01); *A61L 2300/406* (2013.01); *A61L 2300/604* (2013.01); *A61L 2430/02* (2013.01); *A61L 2430/12* (2013.01)

(58) Field of Classification Search
CPC ...... A61K 31/65; A61K 6/0044; A61K 6/027; A61K 6/06; A61K 6/0643; A61K 6/087; A61L 2300/406; A61L 2300/604; A61L 2430/02; A61L 27/12; A61L 27/18; A61L 27/54; A61L 27/58
See application file for complete search history.

(56) References Cited

U.S. PATENT DOCUMENTS

| | | | |
|---|---|---|---|
| 6,425,949 B1 * | 7/2002 | Lemaitre | A61L 24/0015 106/35 |
| 2011/0112654 A1 | 5/2011 | Faldt | |
| 2011/0117197 A1 | 5/2011 | Emanuel et al. | |
| 2015/0202349 A1 | 7/2015 | Emanuel | |

FOREIGN PATENT DOCUMENTS

| | | | | |
|---|---|---|---|---|
| WO | 2010/003696 A2 | 1/2010 | | |
| WO | 2010/007623 A1 | 1/2010 | | |
| WO | WO-2013073935 A1 * | 5/2013 | ............. | A61C 17/20 |
| WO | 2014/020610 A1 | 2/2014 | | |

OTHER PUBLICATIONS

Ansel et al. (Pharmaceutical Dosage Forms and Drug Delivery Systems 7th Edition 1999; Lippincott Williams & Wiliams 7 pages). (Year: 1999).*
Prathapachandran et al. (Dent Res J (Isfahan) 2012;9(5):516-621) (Year: 2012).*
Meffert, RM. (Abstract of: Crit Rev Oral Biol Med. 1996;7(3):278-291; 1 page). (Year: 1996).*
Chadha et al. (J Indian Soc Periodontol 2012;16(2):200-206). (Year: 2012).*
Emanuel, Noam, et al. "A lipid-and-polymer-based novel local drug delivery system—BonyPid™: From physicochemical aspects to therapy of bacterially infected bones." Journal of Controlled Release 160.2 (2012): 353-361.
Elemek E, Almas K. Peri-implantitis: etiology, diagnosis and treatment: an update. The New York state dental journal 2014; 80 (1):26-32.
Mombelli A, Muller N, Cionca N. The epidemiology of peri-implantitis. Clinical oral implants research 2012; 23 Suppl 6:67-76.
Lang NP, Berglundh T. Periimplant diseases: where are we now? Consensus of the Seventh European Workshop on Periodontology. Journal of clinical periodontology 2011; 38 Suppl 11:178-181.
Lee A and Wang HL. "biofilm related to dental implants". Implant Dentistry 2010; 19(5):387-91.
Heitz-Mayfield LJ, Mombelli A. The therapy of peri-implantitis: a systematic review. The International journal of oral & maxillofacial implants 2014; 29 Suppl:325-345.
André Büchter et al. (British Journal of Oral and Maxillofacial Surgery (2004) 42, 454-456.
Willem-Jan Metsemakers, et al. "A doxycycline-loaded polymer-lipid encapsulationmatrix coating for the prevention of implant-related osteomyelitis due to doxycycline-resistant methicillin-resistant *Staphylococcus aureus*." Journal of Controlled Release 209 (2015): 47-56.

(Continued)

*Primary Examiner* — Ernst V Arnold
(74) *Attorney, Agent, or Firm* — Greenberg Traurig, LLP

(57) ABSTRACT

The present invention relates to pharmaceutical compositions and methods for the treatment of peri-implant diseases, in particular peri-implant disease characterized by the destruction of the crest of the alveolar bone supporting the implant. Specifically, the method comprising the step of applying to a peri-implant bone displaying crestal resorption a 5 pharmaceutical composition comprising biocompatible bone augmentation material coated with a matrix composition which provides local controlled and prolonged release of at least one pharmaceutically active agent at the bone loss site.

20 Claims, No Drawings

(56) References Cited

OTHER PUBLICATIONS

Ioannou, I., et al., "The effect of locally delivered doxycycline in the treatment of chronic Periodontitis. A clinical and microbiological cohort study", Journal of Oral & Maxillofacial Research Res 2010 (Oct.-Dec.)|vol. 1|No. 4|e1|pp. 1-12.
Kapoor, A., et al., "Systemic antibiotic therapy in periodontics", Dental Research Journal (Isfahan), Sep.-Oct. 2012, 9(5): pp. 505-515.
Prakasam, A., et al., "Antibiotics in the management of aggressive periodontitis", Journal of Pharmacy & BioAllied Sciences, Aug. 2012, 4(Suppl 2), pp. S252-S255.
Heitz-Mayfield et al., "Comparative biology of chronic and aggressive periodontitis vs. peri-implantitis" Periodontology 2000, vol. 53, No. 1, 167-181.
Rosen et al., "Peri-Implant Mucositis and Peri-Implantitis: A Current Understanding of Their Diagnoses and Clinical Implications", in J Periodontol, Apr. 2013, pp. 436-443.
Lopez-Piriz et al., "Evaluation in a Dog Model of Three Antimicrobial Glassy Coatings: Prevention of Bone Loss around Implants and Microbial Assessments", PLOS One, DOI:10.1371/journal.pone. 0140374, Oct. 21, 2015.
Albrektsson et al "Is marginal bone loss around oral implants a result of provoked foreighn body reaction", Clinical Implant Dentistry and Related Research, vol. 16, No. 2, 2014, pp. 155-165.

Buchter A et al. "Sustained release of doxycycline for the treatment of peri-implantitis: randomized controlled trial" British Journal of Oral and Maxillofacial Surgery (2004) 42, 439-444.
Renvert, S., et al.—"Non-surgical treatment of ped-implant mucositis and ped-implantitis: a literature review", J Clin Periodontol 2008; 35 (Suppl. 8): 305-315 doi: 10.1111/j.1600-051X.2008.01276.x, pp. 305-315.
Shibli, Jamil Awad, et al.—"Is Laser the Best Choice for the Treatment of Peri-Implantitis?", Photomedicine and Laser Surgery, vol. 36, No. 11, 2018, Mary Ann Liebert, Inc., pp. 569-570, DOI: 10.1089/pho.2018.4521.
Tanetti, M.S., et al.—"Primary and secondary prevention of periodontal and peri-implant diseases"—Introduction to, and objectives of the 11th European Workshop on Periodontology consensus conference, J Clin Periodontol 2015; 42 (Suppl. 16): S1-S4 doi: 10.1111/jcpe.12382.
Renvert, S. et al.—"Mechanical and Repeated Antimicrobial Therapy Using a Local Drug Delivery System in the Treatment of Peri-Implantitis: A Randomized Clinical Trial", Journal of Periodontology • May 2008, vol. 79, No. 5, pp. 836-844.
Renvert, Stefan, et al., "Treatment of pathologic pen-implant pockets", Periodontology 2000, vol. 76, 2018, 180-190.
Examiner Interview, "Methods for the Treatment of Peri-Implantitis", U.S. Appl. No. 15/513,163, filed Mar. 24, 2020 (19 pages).

* cited by examiner

METHODS FOR THE TREATMENT OF PERI-IMPLANTITIS

This application claims the benefit of U.S. Provisional application No. 62/059,116, filed Oct. 2, 2015 and entitled "METHODS FOR THE TREATMENT OF PERI-IMPLANT DISEASE", the contents of which are incorporated herein by reference.

FIELD OF THE INVENTION

The present invention relates to methods and pharmaceutical composition for the treatment of peri-implant diseases associated with crestal peri-implant infection and bone loss.

BACKGROUND OF THE INVENTION

Peri-implantitis is characterized by an inflammatory process around an osseo-integrated dental implant, which includes both soft tissue inflammation and progressive loss of supporting bone [Elemek E, Almas K. Peri-implantitis: etiology, diagnosis and treatment: an update. The New York state dental journal 2014; 80 (1):26-32]. The reported prevalence rate of peri-implantitis range from 5% to 47%, depending on the thresholds for probing depth and radiographic bone loss used for disease definition, and the composition of study populations [Mombelli A, Muller N, Cionca N. The epidemiology of peri-implantitis. *Clinical oral implants research* 2012; 23 Suppl 6:67-76.]. If peri-implantitis progresses, it may result in the loss of the implant.

Peri-implantitis is an oral biofilm related disease characterized by changes in the level of the crestal bone in conjunction with bleeding on probing (BoP) with or without concomitant deepening of peri-implant pockets [Lang N P, Berglundh T. Periimplant diseases: where are we now? Consensus of the Seventh European Workshop on Periodontology. Journal of clinical periodontology 2011; 38 Suppl 11:178-181, Lee A and Wang H L. "biofilm related to dental implants". Implant Dentistry 2010; 19(5):387-91].

Currently available treatments of peri-implantitis focus on correcting technical defects by means of surgery and decontamination techniques and were found to have only a limited effect on the clinical signs of peri-implantitis. Non-surgical treatments including a mechanical treatment alone or combined with antiseptics or antibiotics can improve clinical parameters in the short term. Surgical procedures for treating peri-implantitis include access flap and debridement, surgical resection, regeneration with bone grafts, and guided bone regeneration (GBR). In short term follow-up these procedures yield an estimated 2 to 3 mm probing depth reduction, equivalent to 30% to 50% on the initial probing depth. A mean 2 mm radiographic bone fill is achieved with regenerative procedures [Heitz-Mayfield L J, Mombelli A. *The therapy of peri-implantitis: a systematic review. The International journal of oral &maxillofacial implants* 2014; 29 Suppl:325-345].

Regenerative periodontal therapy, using bone grafts, membranes and growth factors, aiming at regenerating a new attachment apparatus and reconstruct the periodontal unit to within previously existing normal physiologic limits, has been used for the treatment of periodontitis. Bone graft substitutes currently available in the market for dental use include ceramic based products (e.g Bio-Oss®) and degradable polymers containing antibacterial drug (e.g. Atridox® which releases doxycycline, Arestin® which releases minocycline, and Actisite® with tetracycline). Atridox, Arestin, and Actisite are indicated for periodontitis treatment, and are used off label in peri-implantitis. Andre Buchter et al. (British Journal of Oral and Maxillofacial Surgery (2004) 42, 454-456) presented a single case study of peri-implantitis treated with a combination of autogenous bone graft with Atridox®. However, Atridox® high burst and the short release period of the antibiotic drug, for no more than several days following the implantation, represent significant limit to their anti-bacterial effect. Furthermore, as indicated above, no satisfactory treatment to peri-implantitis is currently available.

International Publication No. WO 2010/007623 to one of the inventors of the present invention and others, the contents of which are incorporated herein by reference, discloses drug delivery compositions for controlled release of an active ingredient, comprising a lipid-based matrix with a biodegradable polymer. These drug delivery compositions enable to entrap a large variety of one or more biologically active molecules and to release them at a pre-programmed rate for periods ranging from several days to several months.

International Publication No. WO2014/020610 to the inventor of the present invention, the contents of which are incorporated herein by reference, discloses compositions, methods and medical devices for the treatment of open bone fractures comprising the step of applying to a bone void site a composition comprising a matrix which provides local prolonged release of at least one antibiotic agent.

It would therefore be desirable to provide an improved method for the treatment of peri-implantitits which promotes the healing process of the infected mucosal, while enhancing peri-implant bone formation, improve implant survival rates and enhance the oral health-related quality of life.

SUMMARY OF THE INVENTION

The present invention relates to pharmaceutical compositions and methods for the treatment of peri-implant diseases, in particular peri-implant disease characterized by the destruction of the crest of the alveolar bone supporting the implant. Specifically, the method comprising the step of applying to a peri-implant bone displaying crestal resorption a pharmaceutical composition comprising biocompatible bone augmentation material coated with a matrix composition which provides local controlled and prolonged release of at least one pharmaceutically active agent at the bone loss site. The pharmaceutically active agent comprises an antibiotic agent, anti-fungal agent, an anti-inflammatory agent, an antiseptic agent, an agent which induces or stimulates bone growth or a combination thereof. According to some preferred embodiments, the pharmaceutically active agent is antibiotic agent.

The present invention is based in part on the finding that biocompatible bone augmentation material impregnated or coated with a matrix composition comprising an antibiotic agent according to embodiments of the invention, successfully inhibited biofilm formation in-vitro and completely eradicated an in-vitro established biofilm. Oral biofilm is a recognizable etiologic agent of peri-implantitis.

As used herein "peri-implant bone site displaying crestal resorption" refers to any peri-implant bone deficient region, such as a void, gap, recess, or other discontinuity in a peri-implant bone. According to some embodiments, peri-implant bone site displaying crestal resorption is associated with increased peri-implant pocket probing depths. According to some embodiments, peri-implant bone site displaying crestal resorption is characterized by the loss of the bony support of the implant. According to some embodiments, the loss of bony support is accompanied by inflammation.

As used herein, "treatment of peri-implantitis" relates to enhancing peri-implant bone formation. According to some embodiments, treatment of peri-implantitis relates to reduction of pocket probe depth. According to some embodiments, treating peri-implantitis relates to reduction of mucosal recession. According to some embodiments, treating peri-implantitis refers to reduction of bleeding on probing (e.g. bleeding gums or gingival bleeding). According to some embodiments, treating peri-implantitis relates to reducing, or potentially stopping clinical attachment loss. According to some embodiments, treating peri-implantitis relates to the improvement of implant survival rates.

According to one aspect, the present invention provides a method for treating a patient diagnosed with a peri-implant disease comprising the step of implanting at a peri-implant bone a biocompatible bone augmentation material coated with a matrix composition which provides local controlled release of a pharmaceutically active agent selected from the group consisting of an antibiotic agent, an anti-fungal agent, an antiseptic agent, an anti-inflammatory agents, a non-steroidal anti-inflammatory agent, an osteoinductive agent or a combination thereof, at the location at which bone growth is desired. According to some embodiments, the peri-implant disease is associated with crestal peri-implant bone loss. According to a certain embodiment, peri-implant disease is peri-implantitis. According to some embodiments, the step of implanting the pharmaceutical composition of the invention at a peri-implant bone, follows the step of debridement and surface decontamination of the intrabony peri-implantitis defects. According to some embodiments, "implanting at a peri-implant bone" refers to applying the pharmaceutical composition at the gap or void formed between the peri-implant bone and the implant itself.

According to some embodiments, the pharmaceutical composition described herein prevents or inhibits the formation of oral biofilm that may form on the implant and its vicinity. According to some embodiments, the drug coated bone augmentation material disclosed herein is capable of eradicating an existing oral biofilm. The reduction of the bacterial load to a level compatible with health is an important aspect of implant therapy.

Without wishing to be bound by theory or mechanism of action, following its application, the coated bone augmentation material release the pharmaceutically active agent (for example, an antibiotic drug) into the bone site displaying crestal resorption and its surroundings over a pre-set, prolonged, controlled period of time. The bone augmentation material supports osteoconductive bone recovery, and the establishment of intimate bone-to-implant contact while the controlled, prolonged release of the drug from the coating matrix successfully eradicates or prevents bone infection. The antimicrobial activity of the released drug is ancillary to the osteoconductive activity of the bone filler, and prevents its potential rejection or early adsorption by pathogens related oral bone infection.

Thus, the pharmaceutical composition of the invention advantageously combines the pharmaceutical activity (e.g. antibacterial activity) of the released pharmaceutical agent and the osteoconductive activity of the bone augmentation material. Therapeutic amounts of the pharmaceutically active agent are maintained locally at the peri-implant bone loss site, while maintaining low or no detectable synthetic plasma levels.

According to some embodiments, the biodegradable bone augmentation material used in pharmaceutical compositions and methods as disclosed herein is selected from allogeneic (i.e., from human sources), xenogeneic (i.e., from animal sources), synthetic bone augmentation material or any combination thereof. According to some embodiments, the bone augmentation material is mineral based. According to some embodiments the mineral based material is synthetic. According to some embodiments, the bone augmentation material is selected from the group consisting of β-tricalcium phosphate (β-TCP), tetracalcium phosphate, α-tricalcium phosphate (α-TCP), amorphous calcium phosphate, dicalcium phosphate, hydroxyapatite, fluorapatite, oxyapatite, wollastonite, apatite/wollastonite glass ceramics, anorthite, calcium fluoride, calcium sulfate, calcium carbonate, agrellite, devitrite, canasite, phlogopite, monetite, brushite, octocalcium phosphate, whitlockite, cordierite, berlinite, combeite, phosphoric acid crystals, disodium hydrogen phosphate, other phosphate salt-based bioceramics or any combination thereof. According to some embodiments, the bone augmentation material is Tri-Calcium Phosphate (β-TCP), hydroxyapatite or a combination of both. According to some embodiments, the bone augmentation material consists of particles in a form selected from of a block, a cylinder, a granule, a wedge, a trapezoid or any combination thereof. According to some embodiments, the bone augmentation material consists of particles having an average diameter of less than 1000 μm, less than 900 μm, less than 800 μm, less than 700 μm, less than 600 μm, less than 500 μm, less than 400 μm, less than 300 μm, or less than 200 μm. According to some embodiments, the bone augmentation material consists of particles having an average diameter in the range of about 30 to about 800 μm; alternatively, having an average diameter in the range of about 30 to about 700 μm; alternatively, having an average diameter in the range of about 30 to about 500 μm; alternatively, having an average diameter in the range of about 50 to about 500 μm; alternatively, having an average diameter in the range of about 100 to about 500 μm. According to some currently preferred embodiments, the bone augmentation material consists of particles having an average diameter in the range of about 150 to about 500 μm. According to some currently preferred embodiments, the bone augmentation material consists of particles having an average diameter in the range of about 30 to about 150 μm; alternatively, about 50 to about 100 μm.

According to some embodiments, the biocompatible matrix composition used for coating the bone augmentation material is a multi-layered matrix comprising a biocompatible polymer and at least one lipid, wherein the matrix is lipid saturated. Specifically, the matrix composition comprises: (a) biocompatible polymer; (b) a first lipid comprising a sterol (c) a second lipid component comprising at least one phospholipid having fatty acid moieties of at least 14 carbons; and (e) a pharmaceutically active agent.

In some embodiments, the biocompatible polymer comprises a polyester selected from the group consisting of PLA (polylactic acid), PGA (poly glycolic acid), PLGA (poly (lactic-co-glycolic acid)) and combinations thereof. According to other embodiments, the biocompatible polymer is poly ethylene glycol, preferably having a molecular weight of up to 10,000 Dalton. According to some embodiments, the biocompatible polymer constitutes 5-30% of the matrix.

According to some embodiments the first lipid comprises at least one of a sterol. In some embodiments, the sterol is a phytosterol. In some embodiments, the sterol is a zoosterol. According to specific embodiments, the sterol is a cholesterol. In some embodiments, the first lipid component comprises a mixture of sterols. In some embodiments, the first lipid component is substantially free of non-sterol lipids. In some embodiments, the first lipid component constitutes 5-40% (w/w) of the matrix. In some preferred embodiments, the sterol is cholesterol and constitutes up to 50% (w/w) of the total lipid content of said matrix composition. According to particular embodiments the first lipid and polymer are non-covalently associated. In some embodiments, the sterol is cholesterol and constitutes 2-30 mole percent of the total lipid content of said matrix composition.

In some embodiments, the fatty acid moieties of the phospholipid contains at least 12 carbon atoms each. In some embodiments, the fatty acid chains of the phospholipid contains no more than 18 carbon atoms each. In some embodiments, the fatty acid chains of the phospholipid are fully saturated. In some embodiments, at least one of the phospholipid fatty acid chains is non-saturated (e.g. contains at least one double bond). In some embodiments, both phospholipid fatty acid chains are non-saturated. In some embodiments the second lipid comprises a phospholipid selected from the group consisting of a phosphatidylcholine, a mixture of phosphatidylcholines, a phosphatidylethanolamine, and combinations thereof. According to some embodiments the second lipid comprises a mixture of phosphatidylcholines. According to some embodiments the second lipid component further comprises an additional phospholipid selected from the group consisting of a phosphatidylserine, a phosphatidylglycerol, and a phosphatidylinositol. In some embodiments, the second lipid component constitutes 30-80% (w/w) of the matrix composition.

According to some embodiments, the pharmaceutically active agent constitutes 1-20% (w/w) of the matrix composition. According to some embodiments, the pharmaceutically active agent constitutes about 5-15% (w/w) of the matrix composition. According to certain typical embodiments, the pharmaceutically active agent constitutes about 8-12% (w/w) of the matrix composition.

According to some embodiments, the coated bone augmentation material used for treating a patient diagnosed with a peri-implant disease comprises between about 60-90% (w/w) of bone augmentation material and 10-40% (w/w) of the matrix composition described herein. According to some embodiments the coated bone augmentation material comprise between about 70-90% (w/w) of bone augmentation material and 10-30% (w/w) of the matrix composition. According to some embodiments the coated bone augmentation material comprise between about 80-95% (w/w) of bone augmentation material and 5-20% (w/w) of the matrix composition. According to some embodiments the coated bone augmentation material comprise between about 85-90% (w/w) of bone augmentation material and 10-15% (w/w) of the matrix composition. Preferably, the bone augmentation material consists of particles having an average diameter of 500 μm or less. According to some specific embodiments, the coated bone augmentation material contain about 88% (w/w) of β-TCP particles having an average particle size of 150-500 μm coated with about 12% (w/w) of a matrix composition consisting essentially of about 2.4% PLGA, about 1.2% cholesterol, about 5.5% of DPPC, about 1.8% DSPC and about 1.3% doxycycline hyclate.

In some embodiments, the pharmaceutically active agent is incorporated into the matrix composition. According to certain embodiments, the pharmaceutically active agent is an antibiotic agent. According to certain embodiments, the pharmaceutically active agent is an antifungal agent. According to certain embodiments, the pharmaceutically active agent is an antiseptic agent. According to certain embodiments, the pharmaceutically active agent is an anti-inflammatory agent. According to certain embodiments, the pharmaceutically active agent is a steroid or a non-steroidal anti-inflammatory drug. In some embodiment, plurality of pharmaceutically active agents are incorporated into the matrix composition, for example, a combination of two or more antibiotic agents, a combination of one or more antibiotic agents and one or more non-steroidal anti-inflammatory drugs (NSAID). Each possibility represents a separate embodiment of the present invention.

According to some embodiments of the invention, there is provided a pharmaceutical composition comprising a mixture of bone augmentation material coated with a matrix composition and non-coated bone augmentation material. The non-coated bone augmentation material mixed with the coated bone augmentation material of the invention may be the same as the bone augmentation material being coated. For example, the coated and the non-coated bone augmentation material may be both composed of β-TCP. Alternatively, the non-coated bone augmentation material, may be different from the coated bone augmentation material. Alternatively, the pharmaceutical composition may comprise a mixture of non-coated bone augmentation material in addition to the coated particles. According to some embodiments, the pharmaceutical composition of the invention may be mixed with autograft bone material prior to its application to the bone site displaying crestal resorption and its surroundings. According to some embodiments, the weight ratio of the coated to non-coated bone augmentation material in the pharmaceutical composition of the invention is between 1:10 and 10:1. According to some embodiments, the weight ratio of the coated to non-coated bone augmentation material is between 1:5 and 5:1, alternatively between 1:4 and 2:1. According to an exemplary embodiment, the weight ratio of the coated to non-coated bone augmentation material is 1:1. According to some embodiments, the weight of the non-coated bone augmentation material in the pharmaceutical composition of the invention is lower than 90% (w/w) of the total weight of the pharmaceutical composition. According to some embodiments, the weight of the non-coated bone augmentation material in the pharmaceutical composition is lower than 80% (w/w) of the total weight of the pharmaceutical composition. According to some embodiments, the weight of the non-coated bone augmentation material in the pharmaceutical composition is lower than 75% (w/w) of the total weight of the pharmaceutical composition. According to some embodiments, the weight of the non-coated bone augmentation material in the pharmaceutical composition is lower than 70% (w/w) of the total weight of the pharmaceutical composition. According to some embodiments, the weight of the non-coated bone augmentation material in the pharmaceutical composition is lower than 60% (w/w) of the total weight of the pharmaceutical composition. According to some embodiments, the weight of the non-coated bone augmentation material in the pharmaceutical composition is about 50% (w/w) of the total weight of the pharmaceutical composition.

According to certain embodiments, the pharmaceutical composition of the present invention comprises bone augmentation material being impregnated and/or having its surface coated fully or partially with a matrix composition comprising: (a) biodegradable polyester; (b) a sterol; (c) a phosphatidylcholine having fatty acid moieties of at least 14 carbons; and (d) an antibiotic agent. In another embodiment, the matrix composition comprises at least 50% lipids by weight. In another embodiment, the matrix composition is homogeneous.

According to some particular embodiments, the matrix composition comprises: (a) a biodegradable polyester selected from PLA, PGA and PLGA; (b) cholesterol (c) at least one phospholipid having fatty acid moieties of 14-18 carbons; and (d) an antibiotic agent. In some embodiments the biocompatible polyester is PLGA. In some embodiments the composition comprises between 10-30% (w/w) of PLGA. In some embodiments, the phospholipid is a phosphatidylcholine. In some embodiments, the phosphatidylcholine is a mixture of phosphatidylcholines. In some embodiments the phosphatidylcholine(s) have saturated fatty acid moieties, i.e. no carbon-carbon double bonds in the fatty acid chains. In some embodiments the phosphatidylcholine is DPPC, DPSC, DPMC or a combination thereof. In some embodiments the composition comprising a combination of DPPC and DSPC. In some embodiments the weight ratio between DPPC and DSPC is between about 10:1 and 1:1. In some embodiments the antibiotic agent is a tetracycline antibiotic. In some embodiments the tetracycline antibiotic is doxycycline, minocycline or tetracycline. In some embodiments the antibiotic agent constitutes 1-20% (w/w) of the matrix composition.

According to some embodiments of the present invention, the bone augmentation material is coated with the matrix composition, wherein the coatings are of a thickness of 50 µm or less; alternatively, the coatings are of a thickness of 40 µm or less; alternatively, the coatings are of a thickness of 30 µm or less; alternatively, the coatings are of a thickness of 20 µm or less. According to some embodiments, the bone augmentation material is coated with the biodegradable matrix composition, wherein the coatings are of a thickness in the range of 1 µm to 50; alternatively, in the range of 5 µm to 50; alternatively in the range of 5 µm to 40; alternatively in the range of 5 µm to 30; alternatively in the range of 5 µm to 20; alternatively in the range of 10 µm to 20.

According to some typical embodiments of the invention, there is provided a bone augmentation material having a surface at least a portion of which is coated with a matrix composition comprising: (a) a biodegradable polyester selected from PLA, PGA and PLGA; (b) sterol which is non-covalently associated with the polyester; (c) at least one phospholipid having fatty acid moieties of 14-18 carbons; and (d) an antibiotic agent. In some embodiments the phospholipid is a phosphatidylcholine. In some embodiments the phosphatidylcholine is DPPC, DSPC, DMPC, or a combination thereof. In some embodiments the fatty acid moieties are saturated. In some embodiments the phospholipids have fatty acids of 16-18 carbon atoms length. In some embodiments the polyester is PLGA. In some embodiments, the sterol is a cholesterol. In some embodiments the antibiotic agent is selected from doxycycline and rifampicin. In some embodiments the antibiotic agent is doxycycline hyclate. In some other typical embodiments the bone augmentation material is a synthetic bone filler selected from the group consisting of alpha-Tri-Calcium Phosphate (α-TCP), beta-tri-calcium phosphate (β-TCP), hydroxyl apatite, a mixture of α-TCP and β-TCP, or a mixture of any of the foregoing. In some embodiments the bone augmentation material is β-TCP having an average particle size of about 100-500 µm.

In some particular embodiments, the coated bone augmentation material in accordance with an embodiment of the invention comprises (a) 83-90% (w/w) β-TCP; (b) 1.5-4.0% (w/w) PLGA; (c) 0.8-2% (w/w) cholesterol; (d) 4.0-8.0% (w/w) DPPC; (e) 1.0-3.0% (w/w) DSPC; (f) 0.2-2% (w/w) doxycycline.

In some particular embodiments of the invention, there is provided a pharmaceutical composition comprising a mixture of β-TCP particles having an average particle size of about 100 to about 500 µm which are coated in accordance with an embodiment of the invention and non-coated β-TCP particles, preferably having an average particle size of up to about 100 to about 500 µm, said pharmaceutical composition comprising (a) 90-95% (w/w) β-TCP; (b) 1.0-2.0% (w/w) PLGA; (c) 0.4-0.8% (w/w) cholesterol; (d) 2.0-4.0% (w/w) DPPC; (e) 0.7-1.3% (w/w) DSPC; (f) 0.2-2% (w/w) doxycycline. In some embodiments the pharmaceutical composition is for implantation at a peri-implant bone loss site. According to some embodiments, the pharmaceutical composition comprises a combination of coated and non-coated β-TCP having an average particle size of 100-500 µm in a ratio of 1:1.

According to additional particular embodiments, the pharmaceutical composition comprises a combination of coated and non-coated β-TCP at a ratio of 1:1, wherein the total weight ratio between the pharmaceutical composition ingredients is 93-94% (w/w) β-TCP, 1.1-1.5% PLGA, about 0.6-0.7% cholesterol, about 2.7-3.2% DPPC, about 0.8-1.1% DSPC and about 0.4-0.7% doxycycline hyclate. According to certain specific embodiments, the pharmaceutical composition comprises a combination of coated and non-coated β-TCP at a ratio of 1:1, wherein the total weight ratio between the pharmaceutical composition ingredients is 93.5% (w/w) β-TCP, 1.3% PLGA, about 0.65% cholesterol, about 2.94% DPPC, about 0.98% DSPC and about 0.60% doxycycline hyclate. According to some embodiments, the β-TCP particles have an average particle size of 150-500 µm.

According to some embodiments, every 1 gram of a pharmaceutical composition according to embodiments of the present invention, e.g. a plurality of coated β-TCP granules or mixture of coated and uncoated β-TCP granules, comprises between about 0.04 and about 0.2 g doxycycline. According to some embodiments, every 1 gram of the pharmaceutical composition according to embodiments of the present invention comprises between about 0.04 and about 0.1 g of Doxycycline. According to further embodiments, every 1 gram of pharmaceutical composition according to the present invention comprises between about 0.04 and about 0.08 g of Doxycycline.

In some embodiments the plurality of coated bone augmentation material provides local prolonged release of the pharmaceutically active agent at the peri-implant bone loss site. In some embodiments the composition is applied at a dose of 5 grams or lower per peri-implant bone loss site. According to some embodiments, the pharmaceutical composition of the invention is administered at a dose ranging from 0.1-5 grams per one peri-implant bone loss site. It is to be understood that depending on the status of the peri-implant bone loss site (e.g. with respect to pocket probe depth, mucosal recession, bleeding on probing and clinical attachment loss), a higher or a lower dose can be used per one peri-implant bone loss site at the discretion of the skilled in the art. Following the insertion, or implantation of the pharmaceutical composition of the invention into a peri-implant bone loss site, the coated bone augmentation material releases the drug into the bone void and the surrounding over a predetermined, prolonged, controlled period of time. The bone augmentation material scaffold supports osteoconductive bone recovery, by re-absorbing and being replaced by bone during the healing process. In addition, its osteoconductive properties will enhance bone healing, while the controlled, prolonged release of the anti-microbial drug from the coating matrix formulation successfully prevents or eradicates infection of bone and gums surrounding the dental implant. The antimicrobial activity of the released drug is ancillary to the osteoconductive activity of the bone augmentation material, and prevents the development of acute or chronic bone infections following contamination of the dental implant or dental implant surroundings.

According to some embodiments, the pharmaceutical composition is administered to the peri-implant bone loss site directly, in the form of a powder (e.g. in granular form with granules having an average diameter of about 500 µm, preferably 100-500 µm). For ease of application, the pharmaceutical composition may be formulated as a paste (i.e. a colloidal paste) prior to its application to the peri-implant bone loss site. Typically, a paste like structure is obtained by hydrating the pharmaceutical composition of the invention with an aqueous solution prior to its application. According to some embodiments, hydration shall be performed not more than 2 hours prior to the application of the resulting paste to the peri-implant bone loss site, preferably up to 1 hour prior to the application of the resulting paste to the peri-implant bone loss site, more preferably, not more than 30 minutes prior to its application to the peri-implant bone loss site. According to some embodiments, a paste texture will be attained when the amount of aqueous solution (for example: saline) mixed with the drug coated substrates is between 0.1:1 and 1:1 (w/w) respectively; preferably between 0.3:1 and 0.6:1 (w/w) respectively. When applied to the peri-implant bone loss site, the pharmaceutical composition is brought into contact with the implant's surface, the oral bone and surrounding soft tissue and promotes wound healing around a fixture of an implant in the oral cavity, while promoting osteoconductive bone recovery, by re-absorbing and being replaced by bone during the healing process. According to some embodiments, when the bone augmentation material is in granular form with granules having an average diameter of about 150 µm or less, preferably 100 or less, insertion or implantation of the pharmaceutical composition into the peri-implant bone loss site may be performed by injecting the pharmaceutical composition in a non-surgical procedure or through a minimally invasive percutaneous path. Typically, the granules will be hydrated as described above prior to their injection.

According to additional embodiments, the aqueous solution used for hydrating the pharmaceutical composition of the invention prior to its application to the peri-implant bone is a saline solution. According to some embodiments, the aqueous solution comprises a pharmaceutically active agent (e.g. an antibiotic agent), said pharmaceutically active agent may be the same or different from the pharmaceutically active agent within the matrix composition. According to further embodiments, the aqueous solution comprises an antibiotic agent or an agent which induces or stimulates bone growth such as an osteoinductive factor, a growth factor or a combination thereof. According to another embodiment, the aqueous solution comprises an anti-fungal agent, an antiseptic agent, an anti-inflammatory agent, a non-steroidal anti-inflammatory agent or a combination thereof. Without wishing to be bound by any theory or mechanism of action, the aqueous solution mixed with the pharmaceutical composition of the invention, diffuses or permeates into the porous non-coated bone augmentation material. When the aqueous solution further comprises an active agent such as for example an antibiotic agent, the active agent permeated into the porous bone augmentation material is released shortly after the application of the hydrated pharmaceutical composition to the peri-implant bone loss site, thereby obtaining an immediate or short-term release of the antibiotic agent. Thus, by mixing the device of the present invention with an aqueous solution comprising an active agent, a system combining short-term release (e.g. burst release) and long-term or prolonged release of antibiotic pharmaceutically active agent is obtained.

According to some embodiments, the methods of the invention are useful in cases where the peri-implant bone loss site is sterile, contaminated or even infected at the time of implantation of the pharmaceutical composition.

According to some embodiments, the pharmaceutical composition is applied or implanted to conform to the peri-implant bone loss in a patient.

According to some embodiments the pharmaceutical composition of the invention may be applied or implanted together with a dental implant during a dental implant procedure or surgery, for the prevention of the occurrence of a peri-implant disease. According to certain embodiments, the peri-implant disease is peri-implantitis.

The methods of the invention may reduce significantly the time of peri-implant bone healing and rehabilitation and improve implant survival rates. According to some embodiments, the methods of the invention may be used in combination with at least one of the conventional treatments of peri-implantitis. Non-limiting examples of conventional treatments to be used in combination with the methods of the present invention include but are not limited to submucosal debridement; local and/or systemic delivery of antibiotics, submucosal glycine power air polishing, laser treatment and ultrasonic scaling. The methods of the present invention are advantageous over conventional treatments of peri-implantitis as they enable enhanced peri-implant bone formation while treating the inflammatory cell infiltrate in peri-implantitis lesions. It is to be understood, that depending on the status of the peri-implant bone and in particular the amount of crestal peri-implant bone loss, additional treatments comprising additional application of the pharmaceutical composition of the invention at the peri-implant bone loss site might be needed. For example, depending on the amount of the crestal peri-implant bone loss, a second application of the pharmaceutical composition of the invention at the bone lose site can be done at any time after the first treatment, at the decision of qualified physician.

The pharmaceutical composition used in methods according to the invention is applied or implanted locally at the dental bone void by using a spatula, syringe or any other suitable method, with or without the use of membrane coverage.

According to some embodiments, the present invention relates to methods for the treatment of peri-implant diseases characterized by the destruction of the crest of the alveolar bone supporting the implant, the method comprising the following steps:
  a) Mixing a pharmaceutical composition composing a mixture of biocompatible bone augmentation material coated with a matrix composition which provides local controlled and prolonged release of at least one pharmaceutically active agent and uncoated bone augmentation material, wherein the weight ratio between the coated and non coated bone augmentation material is between 1:10 and 10:1, with an aqueous solution wherein the weight ratio between the pharmaceutical composition and the aqueous solution is between 10:1 and 1:1 (w/w).
  b) Applying or implanting the product of step (a) to a peri-implant bone loss site.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

The present invention relates to pharmaceutical compositions and methods for the treatment of peri-implant diseases, in particular peri-implant disease characterized by the destruction of the crest of the alveolar bone supporting the implant. Specifically, the method comprising the step of applying to a peri-implant bone displaying crestal resorption a pharmaceutical composition comprising biocompatible bone augmentation material coated with a matrix composition which provides local controlled and prolonged release of at least one pharmaceutically active agent at the bone loss site. Preferably, the pharmaceutically active agent comprises an antibiotic agent, anti-fungal agent an anti-inflammatory agent, an antiseptic agent, an agent which induces or stimulates bone growth or a combination thereof.

The term "controlled release" refers to control of the rate and/or quantity of pharmaceutically active agent(s) delivered by the matrix compositions of the invention. The controlled release can be continuous or discontinuous, and/or linear or non-linear.

The term "sustained release" means that pharmaceutical active agent is released over an extended period of time.

The term "biofilm" is defined herein in accordance with its regular meaning in the art as a structured community of microorganisms growing attached to a surface and producing a slime layer of extracellular polymers in which the microbial consortia is embedded in a protective environment. The surfaces to which the biofilm is adherent to may be inert or living surfaces (e.g. the implant itself, the peri-implant bone and surrounding soft tissue and necrotic cells). A biofilm community can include bacteria, fungi, yeasts protozoa and other microorganisms.

General Characteristics of the Matrix Composition Used for Substrate Coating

The matrix composition used for impregnating or coating a bone augmentation material according to some embodiments of the invention comprises (a) a biocompatible polymer, (b) a first lipid component comprising at least one sterol which is non-covalently associated with the biocompatible polymer (c) a second lipid component comprising at least one phospholipid having fatty acid moieties of at least 12 carbons; and (d) a pharmaceutically active agent. The matrix compositions provide sustained release of the pharmaceutically active agent at peri-implant bone site displaying crestal resorption in a subject. According to some embodiments, the subject is an individual, a patient, diagnosed with peri-implantitis.

In specific embodiments, the polymer and the lipids form a structurally ordered lipid saturated matrix composition that is substantially free of water. In some embodiments, the matrix composition has a highly organized multilayer structure in which the polymer and lipids are organized in the form of multiple alternating layers. In some embodiments, the biocompatible coating matrix comprises at least about 50% total lipids by weight. In some embodiments, the coating matrix composition comprises at least 40% phospholipids by weight. In some embodiments, the matrix composition comprises at least 10% polymer by weight. In some embodiments, the matrix composition comprises at least 5% antibiotic by weight.

In some embodiments, the matrix composition comprises at least 10% biocompatible polymer by weight. In some embodiments, the matrix composition comprises between about 10-30% polymer by weight. In some embodiments, the matrix composition comprises between about 15-25% polymer by weight. In some embodiments the matrix composition comprises about 20% polymer by weight. In some embodiments the biocompatible polymer constitutes at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), at least 19% (w/w), at least 20% (w/w), at least 21% (w/w), at least 22% (w/w), at least 23% (w/w), at least 24% (w/w), at least 25% (w/w), at least 26% (w/w), at least 27% (w/w), at least 28% (w/w), at least 29% (w/w) or at least 30% (w/w) of the matrix.

According to certain embodiments of the invention, the polymer is a biodegradable polyester. According to some embodiments the polyester is selected from the group consisting of PLA (polylactic acid). "PLA" refers to poly(L-lactide), (poly(D-lactide), and poly(DL-lactide). In another embodiment, the polymer is PGA (polyglycolic acid). In another embodiment, the polymer is PLGA (poly(lactic-co-glycolic acid). The PLA contained in the PLGA may be any PLA known in the art, e.g. either enantiomer or a racemic mixture. The PLGA of methods and compositions of the present invention has, in another embodiment, a 50:50 lactic acid/glycolic acid ratio. In another embodiment, the ratio is 60:40. In another embodiment, the ratio is 75:25. In another embodiment, the ratio is 85:15. In another embodiment, the ratio is 90:10. In another embodiment, the ratio is 95:5. In another embodiment, the ratio is another ratio appropriate for an extended or sustained in vivo release profile. The PLGA may be either a random or block copolymer. Each possibility represents a separate embodiment of the present invention. It is to be emphasized that the polymer may be of any size or length (i.e of any molecular weight).

In another embodiment, the biodegradable polyester may be selected from the group consisting of polycaprolactone, polyhydroxyalkanoate, polypropylenefumarate, polyorthoester, polyanhydride, and polyalkylcyanoacrylate, provided that the polyester contains a hydrogen bond acceptor moiety. In another embodiment, the biodegradable polyester is a block copolymer containing a combination of any two monomers selected from the group consisting of a PLA, PGA, a PLGA, polycaprolactone, a polyhydroxyalkanoate, a polypropylenefumarate, a polyorthoester, a polyanhydride, and a polyalkylcyanoacrylate. In another embodiment, the biodegradable polyester is a random copolymer containing a combination of any two of the monomers listed above. Each possibility represents a separate embodiment of the present invention.

The term "biodegradable" refers to a substance that will degrade over time by hydrolytic action, by the action of enzymes and/or by other similar mechanisms in the human body. "Biodegradable" further includes that a substance can break down or degrade within the body to non-toxic components after or while a therapeutic agent has been or is being released.

According to some embodiments, the polymer is poly ethylene glycol (PEG), preferably a free polyethylene glycol having molecular weight of up to 10,000 Dalton, preferably between 1,000 and 8,000 Dalton, more preferably between 1,000 and 5,000

Dalton.

The term "Biocompatible" refers to a substance that will not cause substantial tissue irritation or necrosis at the target tissue site.

According to some embodiments, the matrix composition comprises up to 40% (w/w) of a first lipid component comprising a sterol which is non-covalently associated with the biocompatible polymer. According to some embodiments, the sterol constitutes up to about 30% (w/w) of the weight of the matrix composition. According to some embodiments, the matrix composition comprises about 5-40% (w/w) of a first lipid component comprising a sterol. According to some embodiments, the matrix composition comprises about 5-30% (w/w) of sterol. According to some embodiments, the matrix composition comprises about 5-20% (w/w) of sterol. According to some embodiments, the matrix composition comprises about 5-15% (w/w) of sterol. According to some embodiments, the matrix composition comprises about 7-13% (w/w) of sterol. According to some embodiments, the matrix composition comprises about 9-11% (w/w) of sterol. According to certain typical embodiments, the matrix composition comprises about 10% (w/w) of sterol. In some embodiments the sterol constitutes at least 5% (w/w), at least 6% (w/w), at least 7% (w/w), at least 8% (w/w), at least 9% (w/w), at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), or at least 19% (w/w) of the matrix. In some embodiments, sterol constitutes not more than 20% (w/w), not more than 19% (w/w), not more than 18% (w/w), not more than 17% (w/w), not more than 16% (w/w), not more than 15% (w/w), not more than 14% (w/w), not more than 13% (w/w), not more than 12% (w/w), not more than 11% (w/w), not more than 10% (w/w), not more than 9% (w/w), not more than 8% (w/w), not more than 7% (w/w), not more than 6% (w/w), or not more than 5% (w/w) of the matrix. According to some currently preferred embodiments, the sterol is cholesterol.

According to some embodiments, the matrix composition comprises at least about 30% (w/w) of a second lipid component comprising at least one phospholipid having fatty acid moieties of at least 12 carbons. According to some embodiments, the matrix composition comprises at least about 40% (w/w) of a second lipid component comprising at least one phospholipid having fatty acid moieties of at least 12 carbons. According to some embodiments, the matrix composition comprises about 40-75% (w/w) of a second lipid component comprising at least one phospholipid having fatty acid moieties of at least 12 carbons. According to some embodiments, the matrix composition comprises about 50-70% (w/w) of a second lipid component comprising at least one phospholipid having fatty acid moieties of at least 12 carbons. According to certain typical embodiments, the matrix composition comprises about 60% (w/w) a second lipid component comprising at least one phospholipid having fatty acid moieties of at least 12 carbons. In some embodiments, the second lipid component comprising at least one phospholipid having fatty acid moieties of at least 12 carbons constitute at least 40% (w/w), at least 45% (w/w), at least 50% (w/w), at least 55% (w/w), at least 60% (w/w), at least 65% (w/w), or at least 70% (w/w), of the matrix. In some embodiments, the second lipid component comprising at least one phospholipid having fatty acid moieties of at least 12 carbons constitute not more than 75% (w/w), not more than 70% (w/w), not more than 65% (w/w) of the matrix. According to some embodiments, the second lipid component comprises at least one phospholipid molecule having fatty acid moieties of at least 14 carbons. According to some embodiments, the second lipid component comprises at least one phosphatidylcholine molecules having fatty acid moieties of at least 14 carbons. According to some embodiments, the phosphatidylcholine molecules of the composition comprise DMPC. According to some embodiments, the phosphatidylcholine molecules of the composition comprise DPPC. According to some embodiments, the phosphatidylcholine molecules of the composition comprise DSPC. According to some embodiments, the matrix composition comprises DOPC. According to some embodiments, the matrix composition comprises a mixture of DOPC with a second phospholipid having fatty acid moieties of at least 14 carbons. According to some embodiments, the matrix composition comprises a mixture of DMPC and DPPC. Typically the ratio between DMPC and DPPC in the formulation is between about 10:1 to 1:10. According to some embodiments, the matrix composition comprises a mixture of DPPC and DSPC. Typically the ratio between DPPC and DSPC in the formulation is between about 10:1 to 1:1; preferably between 5:1 and 2:1; more preferably the ratio between DPPC and DSPC in the formulation is about 3:1. According to some embodiments, the matrix composition comprises about 50-70% (w/w) of a mixture of DMPC and DPPC. According to some embodiments, the matrix composition comprises about 50-70% (w/w) of a mixture of DPPC and DSPC.

In some embodiments, the lipid:polymer weight ratio of a composition of the present invention is between 1:1 and 9:1 inclusive. In another embodiment, the ratio is between 2:1 and 9:1 inclusive. In another embodiment, the ratio is between 3:1 and 9:1 inclusive. In another embodiment, the ratio is between 4:1 and 9:1 inclusive. In another embodiment, the ratio is between 5:1 and 9:1 inclusive. In another embodiment, the ratio is between 6:1 and 9:1 inclusive. In another embodiment, the ratio is between 7:1 and 9:1 inclusive. In another embodiment, the ratio is between 8:1 and 9:1 inclusive. In another embodiment, the ratio is between 1.5:1 and 9:1 inclusive. Each possibility represents a separate embodiment of the present invention.

It is to be emphasized that the sustained release period using the compositions of the present invention can be programmed taking into account the biochemical and/or biophysical properties of the biopolymer and the lipid. Specifically, the degradation rate of the polymer and the fluidity of the lipid should be considered. For example, a PLGA (85:15) polymer will degrade slower than a PLGA (50:50) polymer. A phosphatidylcholine (12:0) is more fluid (less rigid and less ordered) at body temperature than a phosphatidylcholine (18:0). Thus, for example, the release rate of a drug incorporated in a matrix composition comprising PLGA (85:15) and phosphatidylcholine (18:0) will be slower than that of a drug incorporated in a matrix composed of PLGA (50:50) and phosphatidylcholine (14:0). Another aspect that will determine the release rate is the physical characteristics of the entrapped or impregnated drug. In addition, the release rate of drugs can further be controlled by the addition of other lipids into the matrix formulation, some of which are described below.

According to some embodiments, the matrix composition comprises about 1-20% (w/w) of the pharmaceutically active agent. According to some embodiments, the matrix composition comprises about 5-15% (w/w) of the pharmaceutically active agent. According to certain embodiments, the matrix composition comprises about 8-12% (w/w) of the pharmaceutically active agent. According to certain embodiments, the matrix composition comprises about 10% (w/w)

of the pharmaceutically active agent. In some embodiments, the pharmaceutically active agent constitutes at least 1% (w/w), at least 2% (w/w), at least 3% (w/w), at least 4% (w/w), at least 5% (w/w), at least 6% (w/w), at least 7% (w/w), at least 8% (w/w), at least 9% (w/w), at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), or at least 19% (w/w) of the matrix. In some embodiments, the pharmaceutically active agent constitutes not more than 20% (w/w), not more than 19% (w/w), not more than 18% (w/w), not more than 17% (w/w), not more than 16% (w/w), not more than 15% (w/w), not more than 14% (w/w), not more than 13% (w/w), not more than 12% (w/w), not more than 11% (w/w), not more than 10% (w/w), not more than 9% (w/w), not more than 8% (w/w), not more than 7% (w/w), not more than 6 (w/w), not more than 5% (w/w) of the matrix. According to certain embodiments, the pharmaceutically active agent is an antibiotic agent. According to certain embodiments, the pharmaceutically active agent is an antifungal agent. According to certain embodiments, the pharmaceutically active agent is an antiseptic agent. According to certain embodiments, the pharmaceutically active agent is an anti-inflammatory agent. According to certain embodiments, the pharmaceutically active agent is a steroid or a non-steroidal anti-inflammatory drug. In some embodiment, a plurality of pharmaceutically active agents are incorporated into the matrix composition, for example, a combination of two or more antibiotic agents, a combination of one or more antibiotic agents and one or more antifungal agent, a combination of one or more antibiotic agents and one or more non-steroidal anti-inflammatory drugs (NSAID). In some embodiments, the pharmaceutically active agent is incorporated into the matrix composition. Each possibility represents a separate embodiment of the present invention. According to some embodiments, the pharmaceutically active agent has low water solubility. In another embodiment, the pharmaceutically active agent is hydrophobic. In another embodiment, the pharmaceutically active agent is an amphipathic.

The term "hydrophobic" relates to a material, having solubility in distilled water at ambient temperature of less than about 1 gr per 100 ml, or less than about 0.5 gm per 100 ml, or less than about 0.1 gm per 100 ml.

A pharmaceutically active agent having low water solubility as used herein, relates to a material having solubility in distilled water at ambient temperatures of less than about 3 gr per 100 ml, or less than about 2 gr per 100 ml, between 1-2 gr per 100 ml.

According to some embodiments, the pharmaceutically active agent used in methods according to some embodiments of the invention is an antibiotic agent selected from the group consisting of penicillin antibiotics, cephem antibiotics, macrolide antibiotics, tetracycline antibiotics, glycycycline antibiotics, fosfomycin antibiotics, aminoglycoside antibiotics, and new quinolone antibiotics. Non-limiting examples of antibiotic agents include amoxicillin, amoxicillin/clavulanic acid, ampicillin/sulbactam, penicillin, metronidazole, clindamycine, chlortetracycline, dcmeclocycline, oxytetracycline, amikacin, gentamicin, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, claforan, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenamine, nitrofurantoin, pentamidine, rifabutin, rifampin, spectinomycin, tigecycline, trimethoprim, trimetrexate glucuronate, vancomycin, chlorhexidine and carbapenem antibiotics such as ertapenem. According to some embodiments the antibiotic agent is an antibiotic peptide. Each antibiotic represents a separate embodiment of the present invention.

According to some currently preferred embodiments, the antibiotic agent of methods and compositions of the present invention is a tetracycline. In one embodiment, the tetracycline is doxycycline. In another embodiment, the antibiotic is a hydrophobic tetracycline. Non-limiting examples of hydrophobic tetracyclines are 6-demethyl-6-deoxytetracycline, 6-methylene tetracycline, minocycline (also known as 7-dimethylamino-6-demethyl-6-deoxytetracycline), and 13-phenylmercapto-a-6-deoxy-tetracycline. In another embodiment, the antibiotic is selected from the group consisting of doxycycline, tetracycline, and minocycline.

In another embodiment, the antibiotic is doxycycline or doxycycline hyclate. Most importantly, Doxycycline is highly effective against *Staphylococcus aureus* (*S. aureus*), one of the common bacteria causing peri-implantitis. Furthermore, bacteriologic testing indicates appropriate susceptibility to doxycycline by Methicillin-resistant *Staphylococcus aureus* (MRSA). The minimal inhibitory concentrations (MIC) of Doxycycline against common bacteria, as well as such *S. aureus* are relatively low, and can be as low as 0.1 µg/ml (for *S. aureus*), allowing high potency in vivo against oral biofilm related infections such as peri-implantitis.

According to some embodiments, the pharmaceutically active agent used in methods according to some embodiments of the invention is an antifungal agent selected from the group consisting of amphotericin B cholesteryl sulfate complex, natamycin, amphotericine, clotrimazole, nystatin, amphotericin B lipid complex, fluconazole, flucytosine, griseofulvin, itraconazole, ketoconazole, benzoic acid and salicylic acid, betamethasone and clotrimazole, butenafine, carbol-fuchsin, ciclopirox, clioquinol, clioquinol and hydrocortisone, clotrimazole, econazole, gentian violet, haloprogin, iodoquinol and hydrocortisone, ketoconazole, miconazole, naftifine, nystatin, nystatin and triamcinolone, oxiconazole, sodium thiosulfate, sulconazole, terbinafine, tolnaftate, triacetin, undecylenic acid and derivatives thereof, butoconazole, clotrimazole, sulfanilamide, terconazole, and tioconazole.

According to some embodiments, the matrix composition of the invention may comprise, in addition to the antibiotic agent and/or antifungal agent, another pharmaceutically active agent selected from steroids and/or non-steroidal anti-inflammatory drugs (NSAID).

Any suitable NSAID may be integrated into the matrix composition for sustained and/or controlled release. Non limiting examples of NSAID include ibuprofen, flurbiprofen, aminosalicylate sodium, choline magnesium trisalicylate, choline salicylate, diclofenac, diflunisal, etodolac, fenoprofen, indomethacin, ketoprofen, ketolac tromethamine, magnesium salicylate, meclofenamate, mefenamic acid, nabumetone, naproxen, oxaprozin, oxyphenbutazone, piroxicam, salsalate, sulindac and tolmetin. Each NSAID listed represents a separate embodiment of the present invention.

Any suitable steroidal anti-inflammatory drug may be integrated into the matrix composition. Non limiting examples of steroidal anti-inflammatory drugs (SAIDs) to be used in the formulations of the present invention include, but are not limited to, Corticosteroids such as: betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide, cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

In specific embodiments, the matrix composition is substantially free of water. "Substantially free of water" as used herein refers, in one embodiment, to a composition containing less than 5% water by weight. In another embodiment, the term refers to a composition containing less than 4.5% water by weight. In another embodiment, the term refers to a composition containing less than 4.0% water by weight. In another embodiment, the term refers to a composition containing less than 3.5% water by weight. In another embodiment, the term refers to a composition containing less than 3.0% water by weight. In another embodiment, the term refers to a composition containing less than 2.5% water by weight. In another embodiment, the term refers to a composition containing less than 2.0% water by weight. In another embodiment, the term refers to a composition containing less than 1.5% water by weight. In another embodiment, the term refers to a composition containing less than 1.0% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several days, weeks or months.

In another embodiment, the matrix composition is substantially free of unbound water. In another embodiment, the term refers to a composition not containing detectable amounts of unbound water. The term "unbound water"— refers to free water, which is not part of the thin water film (usually a few molecules thick) formed on the surface of macromolecules (e.g. phospholipids and polymers). The total amount of water in the composition may be determined by any method known in the art such as Karl Fischer and loss on drying methods. The ratio between bound and unbound water may be determined for example by differential scanning calorimeter (DSC).

Technology Platform of the bone augmentation material impregnated or coated fully or partially with the matrix composition used in methods of the present invention According to some embodiments, the coating matrix composition has a highly organized multilayer structure in which the polymer and associated cholesterol form one type of layer, the phospholipids form a second type of layer, and the two types of layers are organized in the form of multiple alternating or quasi-alternating layers.

According to some embodiments, the coating matrix composition of the present invention comprises a continuous structure devoid of internal gaps and/or free volume. According to some embodiments, the coating matrix composition is lipid-saturated, indicating that the space between the polymer layers or polymer backbone is filled with lipid molecules in combination the pharmaceutically active agent (e.g. an antibiotic agent and/or antifungal agent), to the extent that additional lipid moieties can no longer be incorporated into the matrix to an appreciable extent.

The coating matrix compositions disclosed herein are lipid saturated. "Lipid saturated," as used herein, refers to saturation of the polymer of the matrix composition with the first lipid component (e.g. cholesterol) and the second lipid component (e.g. phospholipids) in combination with any pharmaceutical agent present in the matrix, and any other lipids that may be present. The matrix composition is saturated by whatever lipids are present. In another embodiment, "lipid saturation" refers to filling of internal gaps (free volume) within the lipid matrix as defined by the external border of the polymeric backbone. The gaps are filled with phosphatidylcholines in combination with cholesterol and possibly other type of lipids and antibiotic agent present in the matrix, to the extent that additional lipid moieties can no longer be incorporated into the matrix to an appreciable extent. Lipid-saturated matrices of the present invention exhibit the additional advantage of not requiring a synthetic emulsifier or surfactant such as polyvinyl alcohol; thus, matrix compositions of the present invention are typically substantially free of polyvinyl alcohol.

In some embodiments, the coating matrix composition is capable of releasing at least 30% of the active agent at zero-order kinetics when it is maintained in an aqueous medium (when it is hydrated). In some embodiments, at least 40% of the pharmaceutically active agent is released from the matrix composition at zero-order kinetics when it is maintained in an aqueous medium. In some embodiments, at least 50% of the pharmaceutically active agent is released from the matrix composition at zero-order kinetics when it is maintained in an aqueous medium. Without being limited by a specific theory or mechanism of action it is suggested that the organized structure or substructure of the matrix composition of the invention is one of the main reasons for the zero-order release rate of the drug or drugs from the matrix formulation following its hydration. Thus, the zero order release rate may be attributed to slow and continuous "peeling" of the hydrated surface layer(s) of the highly organized layers of lipids and polymer, with concomitant release of the drug as the components of the surface layer are removed from the matrix. It is surmised that this process slowly repeats itself, releasing drug(s) at a steady rate over days, weeks or even months, until the matrix has been completely degraded. Without wishing to be bound by theory, it is believed that the polymer form a first type of layer, and that the phospholipid(s) forms a second type of layer, and that these layers alternate i.e. (polymer)-(phospholipid)-(polymer)-(phospholipid); the term "quasi-alternation" is used herein to refer to the situation in which there is alternation of more than one instance of a type of layer, e.g. (polymer)-(phospholipid)-(phospholipid)-(polymer)-(phospholipid)-(phospholipid)-(polymer). It is estimated that the cholesterol molecules are located in between the two layers, the polar head group pointing towards the polymer and the hydrophobic part between the phospholipid molecules.

In some embodiments, the matrix composition has multiple mixed layers of polymer and phospholipid as described supra and it is not in the form of a microsphere, a micelle, a reversed micelle or a liposome. In some embodiments, the matrix composition does not comprise micelles, reverse micelles or liposomes.

According to some embodiments the matrix of the present invention is water resistant. As such water cannot easily, if at all, diffuse into the inner layers of the matrix and the pharmaceutically active agent entrapped between the inner layers cannot easily, if at all, diffuse out of the matrix. More particularly it refers to a composition having its bulk (e.g. part of the composition which is surrounded by an external surface, said external surface is exposed to the surrounding environment) not exposed to water, or exposed to the extent that the amount of penetrating water is small and insufficient to cause matrix bulk disintegration or degradation. Without wishing to be bound by theory or mechanism of action, the water resistance properties of the matrix composition, together with its unique multilayered structure confer the matrix with its sustained release properties, e.g. its ability to release at least 30% of the pharmaceutically active agent (e.g. an antibiotic agent) from the composition at zero order kinetics for periods of time ranging from several days, weeks and even months, when the composition is maintained in an aqueous environment at physiological temperature.

The efficacy of a drug is commonly determined by its local concentration. That, in turn, is determined by the ratio between the accumulation rate of drug released from the product vs. its elimination by physical distribution to surrounding tissue, as well as by neutralization and/or degradation. An optimal drug delivery system should release the drug according to the biological need, in order to create an effective concentration at close proximity to the target and throughout a sufficient period of time needed for the desired biological effect. This can be achieved by releasing the active form of the drug near the target at a rate that will result in an effective concentration that is above the minimal effective rate, but below the toxic level and for the desired period of time needed for effective therapeutic effect.

One of the ways to gain better control over local exposure of a given drug is by controlling its supply rate. The supply rate is dictated by 1) the drug release profile, 2) the release rate and 3) the duration of release. These parameters are closely related; while the release rate is strongly depended on the specific formulation, the duration is a function of two factors: release rate and the size of drug reservoir.

Currently used drug delivery systems typically utilize either polymers or lipids (commonly in the form of liposomes). Whereas a polymer-based drug delivery system features a long lasting release, it often has the drawback of an initial high burst release. On the other hand, while a liposome-based drug delivery system features a low burst release, it often has the drawback of a short lasting release.

The matrix composition of the invention comprising a combination of specific lipids and polymers loaded with a drug, preferably an antibiotic agent, determines not only the release rate profile of the drug, but also allows control over the release rate during a prolonged zero-order kinetic stage. Without wishing to be bound by theory or mechanism of action it is suggested that the most effective drug release profile for eradicating local oral infection will combine initial release, resulting with an effective local concentration of the drug, followed by continuous, zero order kinetics, release over sufficient duration, for example up to 2 months, up to 7 weeks, up to 6 weeks, up to 5 weeks, up to 4 weeks, up to 3 weeks, up to 2 weeks, preferably at least 3-4 weeks ensuring a local concentration of the drug at the peri-implant site that is equal to at least 5 times the MIC of the drug against a specific pathogen (for example *S. aureus*). The initial release should be limited so as to leave sufficient reservoir to support subsequent prolong release.

In some embodiments, when maintained in an aqueous environment, preferably at physiological temperatures, the matrix composition provides an extended or prolonged release of the pharmaceutically active agent over a period of days, weeks or months. In some embodiments, the matrix composition provides an extended release of at least 80% of the pharmaceutically active agent over a period of 5 days; alternatively, at least 80% of the pharmaceutically active agent is released over a period of 10 days; alternatively, at least 80% of the pharmaceutically active agent is released over a period of 15 days; alternatively, at least 80% of the pharmaceutically active agent is released over a period of 20 days; alternatively, at least 80% of the pharmaceutically active agent is released over a period of 25 days; alternatively, at least 80% of the pharmaceutically active agent is released over a period of 30 days. In some embodiments, 1 to 60% of the active agent is released from the matrix composition by the end of the first day, 10 to 100% of the active agent is released from the matrix composition by the end of the first week, 20 to 100% of said active agent is released from the matrix composition by the end of the first two weeks and 30 to 100% of said active agent is released by the end of the first three weeks. In some embodiments, when maintained in an aqueous environment at physiological temperatures, at least 10% but not more than 50% of the active agent is released by the end of the first week, at least 20%, but not more than 75% of the active agent is released by the end of the second week, and at least 30% of the active agent is released by the end of the third week.

According to some exemplary embodiments, bone augmentation material (e.g. tri-calcium phosphate or polyvinyl alcohol) impregnated/coated with a matrix composition comprising about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of doxycycline, displays initial release of up to about 35% of the entrapped antibiotic and preferably up to 30% of the entrapped antibiotic. The amount of drug released immediately post hydration is clinically safe and leaves most of the drug (at least 65%) to prolonged delivery for at least 30 days. and can elevate local concentration of doxycycline to 10-50 MIC or more.

The bone augmentation material impregnated or coated fully or partially with the matrix composition used in methods of the present invention gradually releases the pharmaceutically active agent (e.g. antibiotic agent) at a constant release rate (between about 1.5-5% (weight percent of the pharmaceutically agent released per day/total weight of pharmaceutically active agent initially encapsulated in the matrix composition)), resulting with a local concentration of the drug that is at least 10 times the (minimal inhibitory concentration (MIC) of the antibiotic against pathogens most common is cases of peri-implantitis (e.g. *S. aureus* bacteria) over up to 5 weeks.

Due to the prolonged release characteristics of the pharmaceutical compositions used in methods of the present invention, the therapeutic drug levels can be maintained locally at the peri-implant bone displaying crestal resorption, while maintaining low or no systemic levels. Due to the prolonged local release of the pharmaceutical agent, a small and safe dose of local pharmaceutical agent, which, in some cases, be equal to not more than a single dose commonly administered I.V., may be highly effective in eradicating local bacterial infections in peri-implant bone displaying crestal resorption. By way of example, the amount of antibiotic (e.g. doxycycline) in 1 grams of the pharmaceutical composition comprising a 1:1 combination of non-coated and coated bone augmentation material impregnated or coated fully or partially with the matrix composition used in methods of the present invention is about 1 tenth of the amount of antibiotic in a single dose commonly administered I.V. or a single pill (or tablet) for oral use.

Additionally, the coating matrix composition acts like a reservoir in which the entrapped pharmaceutical agent is protected. In contrast to the conventional polymer based delivery systems, this characteristic can protect sensitive drugs reservoir not only from biological degradation agents such as enzymes, but also from chemical destruction due to in vivo soluble materials and hydration. When prolong effect is needed, this characteristic is becoming highly important.

"Zero-order release rate" or "zero order release kinetics" means a constant, linear, continuous, sustained and controlled release rate of the pharmaceutical active agent from the polymer matrix, i.e. the plot of amounts of pharmaceutical active agent released vs. time is linear. According to some embodiments, at least 30% of the pharmaceutically active agent is released from the matrix composition at zero order kinetics at a rate between about 1-7%, 1.5-6%, 1.5-5%, 2-4%, 1.5-3% (weight percent of the pharmaceutically agent released per day/total weight of pharmaceutically active agent initially encapsulated in the composition), each possibility represent a separate embodiment of the invention.

Lipids

"Phospholipids" are phosphoglycerides having a single phosphatidyl linkage on a glycerol backbone and fatty acids at the remaining two positions. However, it is to be understood explicitly that phosphoglycerides having hydrocarbon chains other than fatty acid residues including alkyl chains, alkenyl chains or any other hydrocarbon chain of at least 12 carbons, alternatively, at least 14 carbons are included within the scope of the present invention. The linkage may be an ether linkage instead of an acyl linkage found in phospholipids.

"Phosphatidylcholine" refers to a phosphoglyceride having a phosphorylcholine head group. This phospholipid is composed of a choline head group and glycerophosphoric acid, with a variety of fatty acids moieties. The fatty acids moieties are typically naturally occurring. In some embodiments, the fatty acid moieties are saturated. In some embodiments, the fatty acid moieties are unsaturated. "Saturated", refers to the absence of a double bond in the hydrocarbon chain. In another embodiment, the fatty acid moieties have at least 12 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both arachidoyl. Each possibility represents a separate embodiment of the present invention.

In another embodiment, the phosphatidylcholine is a naturally-occurring or a synthetic phosphatidylcholine. According to one embodiment, the phosphatidylcholine is a symmetric phosphatidylcholine (i.e. a phosphatidylcholine wherein the two fatty acid moieties are identical (e.g.) dimyristoyl phosphatidylcholine (DMPC), dipalmitoyl-phosphatidylcholine (DPPC), 1,2-distearoyl-sn-glycero-3-phosphocholine (DSPC), dioleoyl-phosphatidylcholine (DOPC). In another embodiment, the phosphatidylcholine is an asymmetric phosphatidylcholine (e.g. 1-palmitoyl-2-stearoyl-phosphatidylcholine (PSPC); 1-palmitoyl-2-oleoyl-phosphatidylcholine (POPC), 1-Stearoyl-2-Arachidonoyl-Phosphatidylcholine (SAPC), 2-Arachidonoyl-1-palmitoyl-sn-glycero-3-phosphocholine (APPC)). In another embodiment, the phosphatidylcholine is any other phosphatidylcholine known in the art. Each phosphatidylcholine represents a separate embodiment of the present invention.

According to certain embodiments, the at least one phosphatidylcholine in coating matrix compositions used in pharmaceutical composition suitable for treating peri-implantitis is selected from the group consisting of DMPC, DPPC, DSPC, DOPC and any combination thereof. Alternatively, the at least one phosphatidylcholine is selected from DMPC, DPPC or a combination thereof. Alternatively, the at least one phosphatidylcholine is selected from DPPC, DSPC or a combination thereof. Alternatively, the at least one phosphatidylcholine is selected from DMPC, DPPC or a combination thereof. Alternatively, the at least one phosphatidylcholine is selected from DMPC, DOPC or a combination thereof.

"Phosphatidylethanolamine" consists of a combination of glycerol esterified with two fatty acids and phosphoric acid. Whereas the phosphate group is combined with ethanolamine. In one embodiments, the fatty acids moieties may be saturated or unsaturated. In another embodiment, the fatty acid moieties have at least 14 carbon atoms. In another embodiment, the fatty acid moieties have at least 16 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. The two fatty acids may be the same, or different, and are usually attached to the 1,2 positions of the glycerol moiety. Non limiting examples of suitable phosphatidylethanolamines are dimethyl dimyristoyl phosphatidylethanolamine (DMPE), dipalmitoyl-phosphatidylethanolamine (DPPE), dilauroylphosphatidylethanolamine (DLPE), distearoylphosphatidylethanolamine (DSPE), dioleoylphosphatidylethanolamine (DOPE), 1-palmitoyl-2-oleylphosphatidylethanolamine (POPE), 1-oleyl-2-palmitoyl-phosphatidylethanolamine (OPPE), and dierucoylphosphatidylethanolamine (DEPE). In another embodiment, the phosphatidylethanolamine is any other phosphatidylethanolamine known in the art. Each phosphatidylethanolamine represents a separate embodiment of the present invention.

"Sterol" in one embodiment refers to a steroid with a hydroxyl group at the 3-position of the A-ring. According to some embodiments, the sterol constitutes up to about 40% (w/w) of the weight of the matrix composition. In another embodiment, the sterol of methods and compositions of the present invention is a zoosterol. In another embodiment, the sterol is cholesterol.

In another embodiment, a composition of the present invention further comprises a lipid other than phosphatidylcholine, phosphatidylethanolamine, or a sterol. In another embodiment, the additional lipid is a phosphoglyceride. In another embodiment, the additional lipid is selected from the group consisting of a phosphatidylserine, a phosphatidylglycerol, and a phosphatidylinositol. In another embodiment, the additional lipid is selected from the group consisting of a phosphatidylserine, a phosphatidylglycerol, a phosphatidylinositol, and a sphingomyelin. In another embodiment, the additional lipid is selected from the group consisting of a phosphatidylserine, a phosphatidylglycerol, a phosphatidylinositol, a sphingomyelin and a ceramide. In another embodiment, a combination of any 2 or more of the above additional lipids is present. In another embodiment, the polymer, phosphatidylcholine, phosphatidylethanolamine, sterol, and additional lipid(s) are all incorporated into the matrix composition. Each possibility represents a separate embodiment of the present invention.

Additional Components

In another embodiment, a matrix composition of methods and compositions of the present invention further comprises a free fatty acid. Non limiting examples of free fatty acids that can be incorporated in the coating matrix composition of the invention are selected from omega-6 fatty acid, omega-9 fatty acid, a free fatty acid having 14 or more carbon atoms, a free fatty acid having 16 or more carbon atoms, a free fatty acid having 16 carbon atoms, a free fatty acid having 18 carbon atoms, a free fatty acid having 16-22 carbon atoms, a free fatty acid having 16-20 carbon atoms, a free fatty acid having 16-18 carbon atoms, a free fatty acid having 18-22 carbon atoms, a free fatty acid having 18-20 carbon atoms, linoleic acid, linolenic acid and oleic acid. In another embodiment, the free fatty acid is another appropriate free fatty acid known in the art. In another embodiment, the free fatty acid adds flexibility to the matrix composition. In another embodiment, the free fatty acid slows the in vivo release rate. In another embodiment, the free fatty acid improves the consistency of the in vivo controlled release. The fatty acid may be unsaturated or saturated. In another embodiment, incorporation of a saturated fatty acid having at least 14 carbon atoms increases the gel-fluid transition temperature of the resulting matrix composition. Each type of fatty acid represents a separate embodiment of the present invention.

In another embodiment, a matrix composition of methods and compositions of the present invention further comprises a tocopherol (e.g. E307 (α-tocopherol), β-tocopherol, E308 (γ-tocopherol), E309 (δ-tocopherol). According to some embodiments, the tocopherol may be incorporated into the matrix instead or in addition to the first lipid having a polar group (e.g. a sterol, a cholesterol). Each possibility represents a separate embodiment of the present invention.

In another embodiment, a matrix composition of methods and compositions of the present invention further comprises physiologically acceptable buffer salts, which are well known in the art. Non-limiting examples of physiologically acceptable buffer salts are phosphate buffers. A typical example of a phosphate buffer is 40 parts NaCl, 1 part KCl, 7 parts $Na_2HPO_4.2H_2O$ and 1 part $KH_2PO_4$. In another embodiment, the buffer salt is any other physiologically acceptable buffer salt known in the art. Each possibility represents a separate embodiment of the present invention.

The present invention relates to pharmaceutical compositions and methods for the treatment of peri-implant diseases, in particular peri-implant disease characterized by the destruction of the crest of the alveolar bone supporting the implant. Specifically, the method comprising the step of applying to a peri-implant bone displaying crestal resorption a pharmaceutical composition comprising biocompatible bone augmentation material coated with a matrix composition which provides local controlled and prolonged release of at least one pharmaceutically active agent at the bone loss site. In some embodiment the matrix composition incorporates a plurality of pharmaceutically active agents. According to some embodiments, the substrate bone augmentation material coated with the matrix composition of the present invention may be administered substantially as a single ingredient (not administered as part of a mixture with other ingredients). Alternatively, it may be applied to the peri-implant bone site as a combination of two or more populations of differently coated bone augmentation material. For example, the methods may comprise the step of applying to the peri-implant bone loss site a combination of a first population of coated bone augmentation material comprising one antibiotic agent mixed with a second population of coated bone augmentation material comprising a different antibiotic agent.

As described above, the amounts, ratios and types of ingredients forming the matrix composition of the present invention may be varied so to adjust the polymer-lipid basis to the biophysical/biochemical properties of the drug, the therapeutically effective dose of the drug and to the desired release rate and/or the duration of release of the drug. The methods of the invention therefore encompass the step of application to the peri-implant bone site of a combination of two or more populations of coated bone augmentation material, each capable of releasing the drug at a different rate and/or duration, the drug in the different coated bone augmentation material populations may be the same or different. Without wishing to be bound by theory or mechanism of action, application to the peri-implant bone site of a combination of coated bone augmentation material populations, each comprising a different drug formulated to be released at a pre-determined rate and/or duration, provides the clinician or skilled artisan with great flexibility in adjusting the treatment protocol according to the medical need. A non-limiting example may be a combination of two populations of drug coated bone augmentation material, one comprising a first antibiotic agent released for about 3-4 weeks and a second population of drug coated bone augmentation material comprising a second antibiotic agent released for about 1-2 weeks.

It is to be emphasized that the bone augmentation material coated/impregnated with a matrix composition according to embodiments of the invention, may be provided to the clinician or skilled artisan as a pre-mixed combination of two or more populations of coated bone augmentation material or preferably, as single ingredients (not part of a mixture with other ingredients) to be mixed by the skilled artisan prior to application to the peri-implant bone site.

Methods of Making Matrix Compositions

In order to obtain the compositions of the invention any suitable method may be employed that will yield a homogeneous dispersion of the polymer and the lipids in a water resistant matrix. Advantageously according to some embodiments the methods employed eschew the use of water at any stage of the manufacturing process.

Advantageously, the matrix compositions of the present invention are prepared by methods which do not involve the formation of emulsions, and may avoid the use of aqueous media altogether. The generation of emulsions that are subsequently dried necessarily results in vesicles or microspheres. In order to produce coated articles the mixture of polymer, lipids and antibiotics within the appropriate selected volatile organic solvents will be used to coat the desired surface.

According to some embodiments the polymer and sterol are mixed with appropriate selected volatile organic solvent(s) on the one hand and the phospholipids together with the active pharmaceutical agent are mixed with its appropriate selected solvent(s) or solvents prior to mixing together with the polymer/sterol mixture.

In certain embodiments, the present invention provides a method of producing a matrix composition, the method comprising the steps of:
(a) mixing into a first volatile organic solvent: (i) a biodegradable polyester and (ii) sterol; and
(b) mixing separately into a second volatile organic solvent: (i) an active agent; (ii) a phosphatidylcholine or a mixture of phosphatidylcholines and optionally (iii) an additional lipid component such as, for example, a phosphatidylethanolamine;
(c) mixing and homogenizing the products resulting from steps (a) and (b); and
(d) bringing the bone augmentation material into contact with the homogenous mixture resulting from step (c).

In another embodiment, phosphatidylethanolamine may be included in the volatile organic solvent of step (a) instead of or in addition to a phosphatidylethanolamine added to the volatile organic solvent of step (b). In another embodiment, the biodegradable polyester is selected from the group consisting of PLA, PGA and PLGA. In another embodiment, the biodegradable polyester is any other suitable biodegradable polyester known in the art. In another embodiment, the polymer is PEG, preferably PEG having molecule weight of up to 10,000 Dalton. In some embodiments the first volatile organic solvent is a non-polar solvent. In some embodiments the second volatile organic solvent is a water miscible solvent. In cases where the active agent is a protein or peptide it is important to select solvents that will not denature or impair the activity of the protein.

In another embodiment, the mixture of step (a) containing a volatile organic solvent is homogenized prior to mixing it with the solution of step (b). In another embodiment, the volatile organic solvent or mixture of volatile organic solvents used in step (a) may be same or different than the volatile organic solvent or mixture of organic solvents used in step (b). In another embodiment, the mixture of step (b) is homogenized prior to mixing it with the mixture of step (a). In another embodiment, the polymer in the mixture of step (a) is lipid saturated. In another embodiment, the matrix composition is lipid saturated. Preferably, the polymer and the phosphatidylcholine are incorporated into the matrix composition. In another embodiment, the active agent as well is incorporated into the matrix composition.

In another embodiment, each step of the production method is substantially free of aqueous solution. In another embodiment, each step is substantially free of the presence of water or any aqueous solution.

Upon mixing, a homogenous mixture is formed. The bone augmentation material to be coated or impregnated with the matrix composition is combined with said homogenous mixture.

The production method further comprises the step of evaporating the solvent present in the product of step (d). Solvent evaporation is typically done by heating the product of step (d). The heating is continuing until the solvent is eliminated and in a typical temperature between room temperature to 60° C., preferably at a temperature below 50° C., more preferably at a temperature of 45° C. or lower, more preferably at a temperature of 30° C. or lower. According to some embodiments, mild vacuum (e.g. 300-600 psi) is applied during the solvent evaporation step. In another embodiment a step of vacuum-drying is performed following the step of solvent evaporation. Each possibility represents a separate embodiment of the present invention.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

The pharmaceutical compositions comprising a mixture of coated and non-coated bone augmentation material described herein above may be equally referred as "medical device" or as a "drug medical device combination".

Example 1: Process for the Preparation of a Bone Augmentation Material Coated/Impregnated with a Matrix Composition According to Certain Embodiments of the Invention Overview: To produce lipid-saturated polymer matrices, two mixtures are created.
1. A biodegradable polymer and a first lipid component (e.g. sterol) are mixed with a volatile organic solvent, which is mixed to yield a solution or suspension of lipid-saturated polymer matrix.
2. The active agent and a second lipid component (e.g. at least one phospholipid) are mixed with a second volatile organic solvent to yield a second solution or suspension.
3. The two solutions or suspensions are combined and mixed until equilibrium is reached.
4. A bone augmentation material is then mixed with the resulting solution of stage 3.
5. The organic solvents are then evaporated, yielding a substrate coated and/or impregnated with a drug-containing, lipid-saturated polymer matrix.

Exemplary Protocol

β-TCP particles having an average diameter of 150-500 μm were coated with a matrix composition suitable for sustained release of doxycycline by the following process:
1. Preparation of Stock Solutions:
1.1. Stock solution of PLGA 75/25 (300 mg/ml in ethyl acetate)—PLGA 75/25 was weighed into volumetric flask. Ethyl acetate was added to volume. The solution was stirred until all PLGA grains were completely dissolved.

1.2. Stock solution of Cholesterol (30 mg/ml in ethyl acetate)—Cholesterol was weighed into volumetric flask. Ethyl acetate was added to volume. The solution was vortexed until the cholesterol was completely dissolved.

1.3. Stock solution of Doxycycline (210 mg/ml in methanol)—Doxycycline was weighed into volumetric flask. Methanol was added to volume. The solution was vortexed until the doxycycline was completely dissolved.

1.4. Stock solution of DPPC (206 mg/ml and DSPC 69 mg/ml in methanol/ethyl acetate mixture (9/14))—DPPC and DSPC were weighed into volumetric flask. Methanol/ethyl acetate (9/14) was added to volume. The solution was incubated at 45° C. for 5 min and vortexed until the phospholipids were completely dissolved.

2. Preparation of the Coating Solution

Solution A—5 volumes of the cholesterol stock solution were mixed with 1 volume of the PLGA stock solution. The mixture contained 50 mg/ml PLGA and 25 mg/ml cholesterol.

Solution B—18 volumes of doxycycline solution were successfully mixed with 82 volumes of phospholipids solution (see section 1.4.). The mixture contained 225 mg/ml phospholipids (56 mg/ml DSPC and 169 mg/ml DPPC) and 37.5 mg/ml doxycycline.

Solution AB—2 volume of solution B were mixed with 3 volumes of solution A resulting solution containing 30 mg/ml PLGA 75/25, 15 mg/ml cholesterol, 90 mg/ml phospholipids and 15 mg/ml doxycycline.

3. Substrate Coating 1.5 gr. of tri-calcium phosphate powder (150-500 μm particles) were weighed into 30 mm glass petri dish.

1.5 ml of solution AB was added to the dish.

The petri dish was placed in a vacuum oven set to 45° C. and partial vacuum was applied ((~610 mm/Hg) until all solvents evaporated (the presence of solvents could not be detected) the oven was turned off and full vacuum was applied to remove any residual solvents (overnight).

The dried coated tri-calcium phosphate powder was transferred into light protected vial and stored at 4° C.

Example 2—Eradication of an Established Biofilm in the Presence of TCP Particles Coated with a Matrix Composition According to Some Embodiments of the Invention The effectiveness of tri-calcium phosphate granules coated with a matrix composition according to embodiments of the invention in eradicating established biofilm was measured using the MBEC™ (Minimum Biofilm Eradication Concentration) Physiology and Genetics Assay.

MBEC™ Test Method Overview: MBEC™ test method specifies the operational parameters required to grow and treat different bacterial biofilms in a high throughput screening assay. The assay device consists of a plastic lid with ninety-six (96) pegs and a corresponding receiver plate with ninety-six (96) individual wells that have a maximum 200 μL working volume. Biofilm is established on the pegs in a batch culture based model (i.e., no flow of nutrients into or out of an individual well) with gentle mixing. The established biofilm is transferred to a new receiver plate for disinfectant efficacy testing.

Sample Description:

Each sample set tested included the following groups listed in the table 1 below:

TABLE 1

| CODE | SAMPLE | DESCRIPTION | Contact time | Concentrations |
|---|---|---|---|---|
| A | β-TCP | Bone graft substitutes; β-Tri Calcium Phosphate (β-TCP) | 24 ± 2 hrs | 0.3%, 1%, 3%, 10% & 30% w/v (mg/μl) so in 200 μL, there is 0.6, 2, 6, 20 and 60 mg of the sample, respectively |
| B | Test-article | Test article formulation: β-TCP granules coated/impregnated with a matrix composition comprising doxycycline hyclate | 24 ± 2 hrs | 0.3%, 1%, 3%, 10% & 30% w/v (mg/μl) so in 200 μL, there is 0.6, 2, 6, 20 and 60 mg of the sample, respectively |
| C | β-TCP + Doxycycline | Doxycycline hyclate non-formulated β-Tri Calcium Phosphate (β-TCP) and free (not formulated) doxycycline hyclate (10 mg/ml and 5 mg/ml solutions in distilled water). | 24 ± 2 hrs | 0.3%, 1%, 3%, 10% & 30% w/v (mg/μl) so in 200 μL, there is 0.006 at 3%, 0.06 at 3%, 0.6, 2, 6, 20 and 60 mg of TCP, respectively that should be impregnated with 6.72, 22.4, 67.2, 224 and 672 μg of the doxycycline, respectively |

Test Organisms: *Staphylococcus aureus* (an osteomyelitis-related strains); source: ATCC 29213; Dilution/Challenge Media: 1,000×TSB+10% human serum 24 hrs; Growth Media/agar: Tryptic Soy Broth/Tryptic Soy agar for 24 hrs Aerobic cond.

TEST METHOD overview: The experimental process for high-throughput antimicrobial susceptibility testing using the hydroxyapatite coated MBEC™ P&G assay. This standard protocol was broken into a series of small steps, each of which is detailed in the sections below.

1. Culture/Inoculum Preparation:

Using a cryogenic stock (at −70° C.), a first sub-culture of *Staphylococcus aureus* was streaked out on OSA (organism specific agar). The plates were incubated at appropriate growth conditions for 20±2.0 hours and further stored at 4° C.

A second sub-culture taken from the first sub-culture was streaked out on OSA. The plates were incubated at appropriate growth conditions for 20±2.0 hours. An isolated colony from the second sub-culture was aseptically removed from the OSA plate and inoculated into 50 mL of sterile bacterial liquid growth broth, followed by incubation appropriate growth conditions for 20±2.0 hours (at 150 rpm).

The inoculum was adjusted to an approximate cell density of $10^6$ CFU/mL by diluting in OSB according to table 1.

Samples (100 μL) of the diluted organism were used for an inoculum check by serially diluting and spot plating on OSA in triplicate.

Preparation of the Challenge Plate:

150 µL of the remaining diluted organism were placed in each of the corresponding wells of an MBEC™ P&G device except the sterility controls (Table 5). The device was placed on an orbital shaker (110 RPM) in a humidified incubator at 37±1° C.

Sample Sterility Controls:

Pegs were broken from BGCH wells with flamed pliers. Each peg was placed into 200 µl, of the neutralizer. The pegs were sonicated for 30 minutes. The recovery suspension was then serially diluted and spot plated on OSA. This served as a biofilm growth check.

200 µL of sterile TSB was added to wells GC and SC-M of the challenge plate, respectively. These served as sterility control (SC) and growth control (GC) for each trial of each organism. BGCh is the biofilm Growth Check. N wells are the neutraliser toxicity controls and N:50 wells are the neutraliser efficacy controls.

Determination of Planktonic MBC:

20 µL from each well of the challenge plate were removed, and placed into the corresponding wells of a fresh 96 well plate containing 180 µL DE neutralizer. The plate was incubated at 35±2° C. for 24±2 hours. MBC results were visually determined post incubation.

$LOG_{10}$ Reduction:

Following sonication, 100 µL from each well of the MBEC™ plate, were put into the first 12 empty wells of the first row of a 96 well-micro titer plate and were further diluted by 10 fold down each of the 8 rows ($10^0$-$10^7$ dilution). 5 µL from each well were then used for spotting prepared OSA plates. The agar plates were incubated at 37±1° C. and counted after approximately 24-48 hours of incubation. The arithmetic mean of the number of colonies counted on the plates was calculated.

100 µL of the sterile neutralizer was added to each well of the recovery plate to top up the volume back to 200 µL. The

TABLE 2

Challenge plate

| | βTCP | | | Test-article | | | β-TCP + Free Doxycycline | | | Gentamicin | | |
|---|---|---|---|---|---|---|---|---|---|---|---|---|
| A | A 30% | A 30% | A 30% | B 30% | B 30% | B 30% | C 30% | C 30% | C 30% | 32 | 32 | 32 |
| B | A 10% | A 10% | A 10% | B 10% | B 10% | B 10% | C 10% | C 10% | C 10% | 16 | 16 | 16 |
| C | A 3.0% | A 3.0% | A 3.0% | B 3.0% | B 3.0% | B 3.0% | C 3.0% | C 3.0% | C 3.0% | 8.0 | 8.0 | 8.0 |
| D | A 1.0% | A 1.0% | A 1.0% | B 1.0% | B 1.0% | B 1.0% | C 1.0% | C 1.0% | C 1.0% | 4.0 | 4.0 | 4.0 |
| E | A 0.3% | A 0.3% | A 0.3% | B 0.3% | B 0.3% | B 0.3% | C 0.3% | C 0.3% | C 0.3% | 2.0 | 2.0 | 2.0 |
| F | SC-A | SC-A | SC-A | SC-B | SC-B | SC-B | A 0.3% (0.06 µg Dox) | A 0.3% (0.06 µg Dox) | A 0.3% (0.06 µg Dox) | 1.0 | 1.0 | 1.0 |
| G | N:50 | N:50 | N:50 | N | N | N | SC-C | SC-C | SC-C | A 0.3% (0.006 µg Dox) | A 0.3% (0.006 µg Dox) | A 0.3% (0.006 µg Dox) |
| H | BGCh | BGCh | BGCh | SC | SC | SC | GC | GC | GC | GC | GC | GC |

Using a sterile 96-well microtitre plate the following was done aseptically to set up the challenge plates listed in Table 2:

Neutralization control: 200 µL of the neutralizer were added to 300 µg of the doxycycline in the N: 50 wells (final concentration of Doxycycline in D/E (neutralizer) is 1.5 mg/mL).

Neutralizer toxicity control: 200 µL of the neutralizer was added to N wells.

Biocide sterility control: 60 mg of β-TCP, test article and β-TCP+Doxycycline were added to SC A-C wells.

Antimicrobial Challenge for Preformed Biofilm:

The biofilm formed on the lid of the MBEC device was rinsed by dipping the lid into saline (~30 seconds) to remove planktonic cells. The lid was then put on top of the challenge plate and incubated on a rotary shaker at 110 rpm at 35±2° C. for 24±2 hours.

Biofilm Recovery:

After incubation (specified above), planktonic cells were rinsed off the biofilm by dipping the lid into saline (~20-30 seconds). The lid was then transferred to a neutralizer/ recovery plate and put in a sonicator (~30 minutes) to dislodge surviving biofilm.

refilled plate is incubated at 35±2° C. for 24±2 hours, after which the plates were analyzed using a plate reader.

The log density for one peg was calculated as follows:

$LOG_{10}$ (CFU/peg)=$LOG_{10}$ [(XB) (D)] where: X=mean CFU; B=volume plated (0.02 mL) and D=dilution.

The overall biofilm accumulation was determined by calculating the mean of the log densities calculated.

$LOG_{10}$ reduction for each dilution was calculated as follows: $LOG_{10}$ Reduction=Mean $LOG_{10}$ Growth Control—Mean $LOG_{10}$ Test Sample.

Results:

Average $LOG_{10}$ CFU/peg recoveries are presented in Table 3:

TABLE 3

Average Log10 CFU/peg recoveries

| | 1 | 2 | 3 | Average | St. Dev |
|---|---|---|---|---|---|
| A | | | | | |
| 30.0% | 3.90 | 3.60 | 3.60 | 3.70 | 0.17 |
| 10.0% | 3.60 | 3.90 | 3.60 | 3.70 | 0.17 |
| 3.0% | 3.60 | 3.78 | 3.60 | 3.66 | 0.10 |

TABLE 3-continued

Average Log10 CFU/peg recoveries

|  | 1 | 2 | 3 | Average | St. Dev |
|---|---|---|---|---|---|
| 1.0% | 3.60 | 3.60 | 3.90 | 3.70 | 0.17 |
| 0.3% | 3.90 | 3.90 | 3.60 | 3.80 | 0.17 |
| B |  |  |  |  |  |
| 30.0% | 0.00 | 0.00 | 0.00 | 0.00 | 0.00 |
| 10.0% | 0.00 | 0.00 | 0.00 | 0.00 | 0.00 |
| 3.0% | 0.00 | 0.00 | 0.00 | 0.00 | 0.00 |
| 1.0% | 1.91 | 2.45 | 0.00 | 1.45 | 1.29 |
| 0.3% | 2.08 | 3.30 | 3.08 | 2.82 | 0.65 |
| C |  |  |  |  |  |
| 30.0% | 0.00 | 0.00 | 0.00 | 0.00 | 0.00 |
| 10.0% | 0.00 | 0.00 | 0.00 | 0.00 | 0.00 |
| 3.0% | 2.90 | 3.20 | 3.08 | 3.06 | 0.15 |
| 1.0% | 3.60 | 3.60 | 3.90 | 3.70 | 0.17 |
| 0.3% | 2.90 | 3.60 | 3.56 | 3.35 | 0.39 |
| D (µg) |  |  |  |  |  |
| 32 | 0.00 | 0.00 | 0.00 | 0.00 | 0.00 |
| 16 | 0.00 | 0.00 | 0.00 | 0.00 | 0.00 |
| 8.0 | 0.00 | 0.00 | 0.00 | 0.00 | 0.00 |
| 4.0 | 1.61 | 2.30 | 0.00 | 1.31 | 1.18 |
| 2.0 | 2.30 | 0.00 | 2.78 | 1.69 | 1.49 |
| 1.0 | 4.72 | 2.60 | 2.30 | 3.21 | 1.32 |
| 0.5 | 3.90 | 2.90 | 3.64 | 3.48 | 0.52 |

Log Reductions are presented in Table 4

TABLE 4

Log Reductions

| Log Reduction | | | % Comp. | Log R | T-test | S/NS |
|---|---|---|---|---|---|---|
| A | Vs. | B | 30.0% | 3.70 | 0.00 | S |
|  |  |  | 10.0% | 3.70 | 0.00 | S |
|  |  |  | 3.0% | 3.66 | 0.00 | S |
|  |  |  | 1.0% | 2.25 | 0.02 | S |
|  |  |  | 0.3% | 0.98 | 0.03 | S |
| A | Vs. | C | 30.0% | 3.70 | 0.00 | S |
|  |  |  | 10.0% | 3.70 | 0.00 | S |
|  |  |  | 3.0% | 0.60 | 0.00 | S |
|  |  |  | 1.0% | 0.00 | 0.50 | NS |
|  |  |  | 0.3% | 0.45 | 0.07 | NS |
| GC | Vs. | D | 32 | 4.59 | 0.00 | S |
|  |  |  | 16 | 4.59 | 0.00 | S |
|  |  |  | 8.0 | 4.59 | 0.00 | S |
|  |  |  | 4.0 | 3.29 | 0.00 | S |
|  |  |  | 2.0 | 2.90 | 0.00 | S |
|  |  |  | 1.0 | 1.38 | 0.02 | S |
|  |  |  | 0.5 | 1.11 | 0.00 | S |

MBC and MBEC Visual Reading data is presented in Table 5

TABLE 5

MBC and MBEC Visual Reading data

|  | 1 | 2 | 3 | 4 | 5 | 6 | 7 | 8 | 9 | 10 | 11 | 12 |
|---|---|---|---|---|---|---|---|---|---|---|---|---|
| MBEC |  |  |  |  |  |  |  |  |  |  |  |  |
| A | + | + | + | − | − | − | − | − | − | − | − | − |
| B | + | + | + | − | − | − | − | − | − | − | − | − |
| C | + | + | + | − | − | − | + | + | + | − | + | − |
| D | + | + | + | − | − | − | + | + | + | − | + | + |
| E | + | + | + | + | + | + | + | + | + | − | + | + |
| F | − | − | − | − | − | + | + | + | + | + | + | + |
| G | + | + | + | + | + | + | − | − | − | + | + | + |
| H | − | − | − | − | − | − | + | + | + | + | + | + |

TABLE 5-continued

MBC and MBEC Visual Reading data

|  | 1 | 2 | 3 | 4 | 5 | 6 | 7 | 8 | 9 | 10 | 11 | 12 |
|---|---|---|---|---|---|---|---|---|---|---|---|---|
| MBC |  |  |  |  |  |  |  |  |  |  |  |  |
| A | + | + | + | − | − | − | − | − | − | − | − | − |
| B | + | + | + | − | − | − | − | − | − | − | − | − |
| C | + | + | + | − | − | − | − | − | − | − | − | − |
| D | + | + | + | − | − | − | − | − | − | − | + | + |
| E | + | + | + | − | − | − | − | − | − | − | + | + |
| F | − | − | − | − | − | − | − | − | − | + | + | + |
| G | + | + | + | + | + | + | − | − | − | + | + | + |
| H | − | − | + | − | − | − | + | + | + | + | + | + |

Conclusion: The log reduction data indicated that the test article (TCP granules coated with a matrix composition according to embodiments of the invention) managed to kill a preformed biofilm at a minimum concentration of 3.0% and was effective even at 1.0% (>99% kill). In contrast, the non-formulated doxycycline with β-TCP was effective at concentrations of 10% or above.

Example 3—Inhibition of Biofilm Formation in the Presence in the Presence of TCP Particles Coated with a Matrix Composition According to Some Embodiments of the Invention The effectiveness of tri-calcium phosphate granules coated with a matrix composition according to embodiments of the invention in inhibiting biofilm formation was evaluated by calculating the bacterial log reduction values using the MBEC™ (Minimum Biofilm Eradication Concentration) Physiology and Genetics Assay (The system is described above in EXAMPLE 2).

Culture/Inoculum preparation followed the procedure described above in Example 1.

Preparation of the Challenge Plate:

TABLE 6

Challenge plate design: SC wells are sterility controls for each experiment. GC is the growth control. BGCh is the biofilm Growth Check. N wells are the neutralizer toxicity controls. N:50 wells are the efficacy controls.

*Staphylococcus aureus*

|  | 1 | 2 | 3 | 4 | 5 | 6 | 7 | 8 | 9 |
|---|---|---|---|---|---|---|---|---|---|
| A | SC-A | SC-A | SC-A | B1 | B1 | B1 | A1 | A1 | A1 |
| B | SC-B | SC-B | SC-B | B2 | B2 | B2 | A2 | A2 | A2 |
| C | N:50 | N:50 | N:50 | B3 | B3 | B3 | A3 | A3 | A3 |
| D | N | N | N | B4 | B4 | B4 | A4 | A4 | A4 |
| E |  |  |  | B5 | B5 | B5 | A5 | A5 | A5 |
| F |  |  |  |  |  |  |  |  |  |
| G |  |  |  |  |  |  |  |  |  |
| H | BGCh | BGCh | BGCh |  |  |  |  |  |  |

Using a sterile 96-well microtitre plate the following was done aseptically to set up the above challenge plates:

Efficacy control: 150 µL of the neutralizer was added to 672 µg of the doxycycline in the N: 50 wells (final concentration of Doxycycline in D/E was 4.48 mg/mL).

Neutralizer toxicity control: 150 µL of the neutralizer was added to N wells.

Biocide sterility control: 60 mg of the test-article were added to SC wells.

60 mg of each of TCP and test-article were added as in the layout of Table 9 in columns 1-9 (n=3).

1504 of the inoculated media were added to each well of the biofilm formation/challenge 96 well plate except for the sterility controls.

Antimicrobial Challenge for Biofilm Formation Inhibition:

The lid was transferred to the challenge plate and incubated on a rotary shaker at 110 rpm at 35±2° C. for 24±2 hours.

Planktonic cells were rinsed from the biofilm that have formed on the lid of the MBEC device by dipping the lid into a rinse plate (2004 of saline per well) for 30 seconds.

After the specified contact time, the MBEC™ lid was transferred to the neutralizer plate (200 µL of neutralizer per well).

The plate was placed in the sonicator and sonicated for 30 minutes to dislodge surviving biofilm.

Determination of planktonic MBC and $LOG_{10}$ Reduction were done as described above in Example 1.

Average $LOG_{10}$ recovery is summarized in Table 7 below.

TABLE 7

Average $LOG_{10}$ recovery

|  | 1 | 2 | 3 | Average | StDev |
|---|---|---|---|---|---|
| A |  |  |  |  |  |
| 30.0% | 4.60 | 5.38 | 4.90 | 4.96 | 0.39 |
| 10.0% | 5.30 | 5.56 | 5.45 | 5.43 | 0.13 |
| 3.0% | 4.90 | 5.30 | 5.08 | 5.09 | 0.20 |
| 1.0% | 5.38 | 5.51 | 5.60 | 5.50 | 0.11 |
| 0.3% | 5.60 | 5.20 | 5.60 | 5.47 | 0.23 |
| B |  |  |  |  |  |
| 30.0% | 0.00 | 0.00 | 0.00 | 0.00 | 0.00 |
| 10.0% | 0.00 | 0.00 | 0.00 | 0.00 | 0.00 |
| 3.0% | 0.00 | 0.00 | 0.00 | 0.00 | 0.00 |
| 1.0% | 0.00 | 0.00 | 0.00 | 0.00 | 0.00 |
| 0.3% | 0.00 | 0.00 | 0.00 | 0.00 | 0.00 |

Log Reductions are presented in Table 8

TABLE 8

$LOG_{10}$ reduction

| Log Reduction |  |  | % Comp. | LogR | Ttest | S/NS |
|---|---|---|---|---|---|---|
| A | Vs. | B | 30.0% | 4.96 | 0.00 | S |
|  |  |  | 10.0% | 5.43 | 0.00 | S |
|  |  |  | 3.0% | 5.09 | 0.00 | S |
|  |  |  | 1.0% | 5.50 | 0.00 | S |
|  |  |  | 0.3% | 5.47 | 0.00 | S |

MBC and MBEC Visual Reading data is presented in Table 9:

TABLE 9

MBC and MBEC Visual Reading data

|  | 1 | 2 | 3 | 4 | 5 | 6 | 7 | 8 | 9 |
|---|---|---|---|---|---|---|---|---|---|
| MBC |  |  |  |  |  |  |  |  |  |
| A | − | − | − | − | − | − | + | + | + |
| B | − | − | − | − | − | − | + | + | + |
| C | − | − | − | − | − | − | + | + | + |
| D | + | + | + | − | − | − | + | + | + |
| E | + | + | + | − | − | − | + | + | + |
| F |  |  |  |  |  |  |  |  |  |
| G |  |  |  |  |  |  |  |  |  |
| H |  |  |  |  |  |  |  |  |  |

TABLE 9-continued

MBC and MBEC Visual Reading data

|  | 1 | 2 | 3 | 4 | 5 | 6 | 7 | 8 | 9 |
|---|---|---|---|---|---|---|---|---|---|
| MBEC |  |  |  |  |  |  |  |  |  |
| A | − | − | − | − | − | − | + | + | + |
| B | − | − | − | − | − | − | + | + | + |
| C | − | − | − | − | − | − | + | + | + |
| D | + | + | + | − | − | − | + | + | + |
| E | + | + | + | − | − | − | + | + | + |
| F |  |  |  |  |  |  |  |  |  |
| G |  |  |  |  |  |  |  |  |  |
| H | + | + | + |  |  |  |  |  |  |

Conclusions: The A control compound (TCP only) had good recovery and growth over the duration of the challenge and at all tested concentrations of TCP.

The B Test compound completely killed the bacteria that was inoculated into the test wells at every concentration tested. The MBC data indicates that all the cells were killed and not simply inhibited at the tested concentrations.

Example 4: Pre-Clinical Study of the Effectiveness of the Pharmaceutical Composition According to Certain Embodiments of the Invention in the Treatment of Peri-Implantitis Study Design:

Study involves 2-4 dogs.

Each dog is implanted with 6 implants, placed at the bone level.

Peri-Implantitis is induced such that 4 mm of bone is lost. Bone loss pattern should result with a "saucer" that leaves at least 270' of bone around the each implant, with vertical loss of up to 2 mm from implant's head.

Surgical treatment includes debridement following conventional protocols, removal of infected tissue but not bone, and augmentation of site with the pharmaceutical composition according to certain embodiments of the invention or with a non-coated β-Tricalcium Phosphate granules Outcomes evaluated:
1. Gross Pathology of the sites.
2. Radiographic appearance of each implant.
3. Histological analysis of formed bone (amount, maturity, level relative to implants' head, closeness to implant etc.) and re-Osseointegration to the infected implant surfaces.

Example 5: A Pilot, Randomized, Open Label, Two Arm Controlled Study for Safety and Efficacy of Implantation of a Pharmaceutical Composition According to Certain Embodiments of the Invention in Patients Suffering from Peri-Implantitis Defects A pilot, randomized, open label, two arm controlled, study for safety and efficacy evaluation of a pharmaceutical composition according to certain embodiments of the invention in patients undergoing surgical treatment for intrabony peri-implantitis defects.

Implants are particularly susceptible to surface colonization of bacteria. The presence of bacteria in the bone stimulates the immune system and triggers an inflammatory process. Consequently, the immune system stimulates osteoclasts activity, which results in osseous resorption. The aim of peri-implantitis treatment is to stop the bone loss progression by controlling the bacterial infection and per-implant tissue inflammation.

The pharmaceutical composition used in the present study provides a porous scaffold upon which bone formation can occur. In addition, it is coated with a matrix composition designed for local sustained release of Doxycycline hyclate which allows the βTCP granules osteoconductive activity to transpire in bones that are contaminated by preventing early osseous tissue resorption that is triggered by inflammatory process.

Pharmaceutical Composition Description:

a mixture (1:1 ratio in mass) of biodegradable β-Tricalcium Phosphate (β TCP) granules having an average size in the range of 150-500 μm (Kasios®) and of identical granules that are coated with a matrix composition comprising about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of doxycycline hyclate. More specifically, the total weight ratio between the pharmaceutical composition ingredients is 93-94% (w/w) β-TCP, 1.1-1.5% PLGA, about 0.6-0.7% cholesterol, about 2.7-3.2% DPPC, about 0.8-1.1% DSPC and about 0.4-0.7% doxycycline hyclate.

The total percentage of Doxycycline hyclate in said 1:1 mixture is about 0.65% which is equivalent to 0.56% Doxycycline. It is supplied sterile and is intended for single use. Doxycycline:_Doxycycline is a member of the tetracycline antibiotics group, and is an effective and highly potent broad spectrum antibiotic. Its high potency and the relatively rare resistance to Doxy by S.aureus are highly beneficial in treating or preventing bone infections. The overall safety profile of Doxy, as well as the experience in treating bone related infections in the clinic, justifies the use of this potent antibiotic as the first choice in the pharmaceutical composition according to certain embodiments of the invention.

The antibacterial activity of the released antibiotic is ancillary to the osteoconductive activity of the bone augmentation material, and prevents its potential rejection or early absorption by bacteria related local bone infection.

All enrolled subjects will undergo similar assessments as follows:

Visit 1, 2-6 Weeks before treatment—Screening/Run-in period

Subjects will undergo screening assessments including the following:
  Preparatory routine treatment including mechanical debridement of teeth and implants using hand instruments for teeth and implants.
  A standard parallel bitewing type radiographs (e.g. held with a RINN holder) for evaluation of eligibility and in particular to select the target implant with radiographic intrabony defect, bone loss of ≥3 mm, and minimum of 2 mm of bone at implant apex. Bone level is measured on mesial and distal projections of the target implant (calculated from implant's shoulder).
  Clinical parameters are measured at four sites per implant (mid sections of mesial, buccal, distal and lingual areas). Measurements are performed utilizing identical Hu-Friedy UNC15 probes. Probing force ranges from 0.15 to 0.25 N.
  Recordation of the following clinical parameters:
    a) Clinical Attachment Level (CAL)—the distance from the implant shoulder to the base of the pocket/sulcus
    b) Bleeding on Probing (BoP)—mean number of BoP positive sites around the implant
    c) Pocket Probing Depth (PPD)—the distance from the gingival margin to the base of the pocket.
    d) Mucosal Recession (REC)—the distance from the implant shoulder to the free gingival margin (CAL-PPD)
    e) Full Mouth Plaque Score (FMPS)—the percentage of sites where plaque is present divided by the number of sites examined The clinical parameter measurements are used to select the target implant with PPD within the following range: 8 mm≤PPD≥5 mm, and bleeding on probing with or without suppuration.

Visit 2, Day 0—Procedure Day Procedure/assessment conducted prior to surgery include:
  Bitewing radiography of the target implant for baseline bone level measurement. Bone level is measured on mesial and distal projections of the target implant (calculated from implant's shoulder).
  Baseline measurement of clinical parameters: CAL, BoP, PPD, REC, and FMPS.

Eligible subject is randomly assigned into Treatment or Control group in a 1:1 ratio, as follows:
  Treatment group: Manual debridement and/or surface decontamination of the intrabony periimplantitis defects followed by device implantation.
  Control group: Manual debridement and/or surface decontamination of the intrabony periimplantitis.

Only one dental implant per subject is randomized and included in the clinical investigation. Non target implants are treated as control group, without inclusion in the study.

Surgery follows standard surgical procedures for periimplantitis, including manual debridement and surface decontamination.

Post-surgery procedures/assessments include:
  Recording of any local or systemic adverse events, including any change in medical or dental status
  Recording of concomitant medications, if any
  Prescribing of post-operative systemic antibiotics for 7 days (amoxicillin or clindamycin) as well as a Chlorhexidine mouth rinses for two weeks.

Visits 3-9, up to 12 months—Follow-up Period

At the follow-up period, subject undergoes clinical evaluation at suture removal or two weeks post implantation (whatever comes first), and 3, 6, 9 and 12 months post implantation.

The following assessments post-surgery are conducted:
Two weeks post-surgery: Suture removal, AE, and concomitant medications recording.

3 months post-surgery: CAL, REC, PPD, BoP, FMPS, AE and concomitant medications recording, and dental hygienist cleaning.

6 months post-surgery: Bitewing radiograph for the target implants, BL, CAL, PPD, REC, BoP, FMPS, AE and concomitant medications recording, and dental hygienist cleaning.

9 months post-surgery: AE and concomitant medications recording, and dental hygienist cleaning.

12 months post-surgery: Bitewing radiograph for the target implants, BL, CAL, PPD, REC, BoP, FMPS, AE and concomitant medications recording, and dental hygienist cleaning.

Inclusion Criteria
  Men and women of age 18-80 years at screening.
  Minimum of one Osseo-integrated implant with periimplantitis.
  Selected implant with PPD within the following range: 8 mm≤PPD≥5 mm
  Bleeding on probing of selected implant with or without suppuration Selected implant with radiographic:
a. Intrabony defect
b. Bone loss of ≥3 mm.
c. Minimum of 2 mm of bone at implant apex Exclusion Criteria Patients presenting severe active periodontitis.
Patient with poor oral hygiene
Selected implant with radiographic evidence of horizontal bone loss only.
Patients suffering from diabetes
Pregnant women or women who intend to become pregnant during the study period.
Lactating women.
Patients with known allergy or contra indications to tetracycline(s)
Heavy smokers (define more than 1 pack/day).
Subjects who were under oral or local antibiotic therapy in the last 4 weeks prior study entry.
Subjects treated for at least 2 weeks with any medication known to affect soft tissue condition within one month prior to baseline examination (i.e. Phenytoin, cyclosporine, Coumadin and NSAIDs).
Presence of active systemic infectious diseases such as: hepatitis, HIV, history of tuberculosis.
Patients who have a clinical significant or unstable medical or surgical condition that may preclude safe and complete study participation as determined by medical history based on the opinion of the investigator.

Effectiveness of the implanted pharmaceutical composition is assessed by:
a. Clinical and radiographical factors (pocket depth, bleeding on probing and bone levels) around implants treated with the pharmaceutical composition versus implants treated with a conventional bone augmentation material (β-TCP).
b. The ability of the pharmaceutical composition to induce re-Osseointegration to previously infected implant surface.

The invention claimed is:

1. A method for treating a patient suffering from peri-implantitis comprising:
   surgically exposing the dental implant in a peri-implant bone loss site in the patient;
   debriding and decontaminating the exposed dental implant; and
   applying once to the peri-implant bone loss site a dose ranging from 0.1-2 grams of a pharmaceutical composition comprising a biocompatible bone augmentation material coated with a matrix composition,
   wherein the matrix composition comprises:
   (a) a biocompatible polymer;
   (b) a first lipid comprising at least one sterol;
   (c) a second lipid comprising at least one phospholipid having fatty acid moieties of at least 14 carbons; and
   (d) at least one pharmaceutically active agent,
   wherein the at least one pharmaceutically active agent comprises doxycycline or doxycycline hyclate at 0.4-2% (w/w) of the total weight of the pharmaceutical composition, and
   wherein said matrix composition provides local sustained release of the pharmaceutically active agent at the pen-implant bone loss site, thereby reducing peri-implantitis defects in the peri-implant bone loss site.

2. The method of claim 1, wherein the pen-implant disease is further associated with at least one of clinical attachment loss and extensive mucosal recession and/or bleeding on probing.

3. The method of claim 1, wherein the bone augmentation material is selected from the group consisting of allogeneic, xenogeneic, synthetic bone augmentation materials or any combination thereof.

4. The method of claim 1, wherein the bone augmentation material comprises beta tri-calcium phosphate (β-TCP) particles.

5. The method of claim 1, wherein the bone augmentation material comprises particles having an average particle size of up to about 500 μm inclusive.

6. The method of claim 1, wherein the coated bone augmentation material comprises between about 80-90% (w/w) of bone augmentation material and between about 10-20% (w/w) of the matrix composition.

7. The method of claim 1, wherein the pharmaceutical composition further comprises non-coated bone augmentation material.

8. The method of claim 7, wherein the weight ratio between the coated bone augmentation material and the non-coated bone augmentation material is between about 1:3 and about 10:1.

9. The method of claim 1, wherein the biocompatible polymer is a biodegradable polyester selected from the group consisting of PLA, PGA and PLGA.

10. The method of claim 9, wherein the biodegradable polyester is present at a weight percentage of up to 2% (w/w) of the total weight of the pharmaceutical composition.

11. The method of claim 1, wherein the sterol comprises cholesterol.

12. The method of claim 11, wherein the cholesterol is present at a weight percentage of up to 0.8% (w/w) of the total weight of the pharmaceutical composition.

13. The method of claim 1, wherein the pharmaceutically active agent further comprises an anti-inflammatory agent.

14. The method of claim 1, wherein the pharmaceutical composition comprises a plurality of antibiotic agents.

15. The method of claim 1, wherein the pharmaceutically active agent is present at 0.4-0.8% (w/w) of the total weight of the pharmaceutical composition.

16. The method of claim 1, wherein the pharmaceutical composition further comprises an additional active agent which induces or stimulates bone growth.

17. The method of claim 1, wherein the second lipid comprises a phosphatidylcholine selected from the group consisting of DMPC, DPPC, DSPC, DOPC or any combination thereof.

18. The method of claim 17, wherein the weight of the combination of phosphatidylcholines constitutes at least 2.5% (w/w) of the total weight of the pharmaceutical composition.

19. A method for treating an oral biofilm at a peri-implant site of a patient, the method comprising:
   surgically exposing the dental implant at the pen-implant site in the patient;
   debriding and decontaminating the exposed dental implant; and
   applying once to a pen-implant bone site a dose ranging from 0.1-2 grams of a pharmaceutical composition comprising a biocompatible bone augmentation material coated with a matrix composition,
   wherein the matrix composition comprises:
   (a) a biocompatible polymer;
   (b) a first lipid comprising at least one sterol;
   (c) a second lipid comprising at least one phospholipid having fatty acid moieties of at least 14 carbons; and
   (d) at least one pharmaceutically active agent, wherein the at least one pharmaceutically active agent comprises doxycycline or doxycycline hyclate at 0.4-0.8% (w/w) of the total weight of the pharmaceutical composition, and wherein said matrix composition provides local sustained release of the pharmaceutically active agent at the pen-implant site.

20. A method for treating a patient suffering from peri-implantitis associated with crestal peri-implant bone loss comprising: surgically exposing the dental implant in the peri-implant bone loss site in the patient; debriding and decontaminating the exposed dental implant; and applying to a pen-implant bone loss site a pharmaceutical composition comprising coated and non-coated bone augmentation material at a ratio of between about 1:3-10:1, wherein the coated bone augmentation material comprises between about 80-90% (w/w) of bone augmentation material coated with between about 10-20% (w/w) of a matrix composition which comprises:

(a) 15-25% (w/w) poly (lactic-co-glycolic acid) (PLGA);
(b) 5-15% (w/w) of cholesterol;
(c) 50-70% (w/w) of a mixture of 1,2-dipalmitoyl-sn-glycero-3-phosphocholine (DPPC) and 1,2-distearoyl-sn-glycero-3-phosphocholine (DSPC), wherein the ratio of DPPC to DSPC is between 5:1 and 2:1 and (d) 7-12% (w/w) of doxycycline or doxycycline hyclate.

* * * * *